United States Patent
Lamb et al.

(10) Patent No.: US 10,669,499 B2
(45) Date of Patent: Jun. 2, 2020

(54) ETHER COMPOUNDS AND RELATED COMPOSITIONS

(71) Applicant: CASTROL LIMITED, Pangbourne, Reading (GB)

(72) Inventors: Gordon Lamb, Naperville, IL (US); Amit Gokhale, Naperville, IL (US); John Philip Davies, Naperville, IL (US); John Redshaw, Naperville, IL (US); Peter Seden, Naperville, IL (US); Kevin West, Naperville, IL (US)

( * ) Notice: Subject to any disclaimer, the term of this patent is extended or adjusted under 35 U.S.C. 154(b) by 47 days.

(21) Appl. No.: 15/579,788

(22) PCT Filed: Jun. 17, 2016

(86) PCT No.: PCT/IB2016/000943
§ 371 (c)(1),
(2) Date: Dec. 5, 2017

(87) PCT Pub. No.: WO2016/203310
PCT Pub. Date: Dec. 22, 2016

(65) Prior Publication Data
US 2018/0163150 A1 Jun. 14, 2018

Related U.S. Application Data

(60) Provisional application No. 62/181,536, filed on Jun. 18, 2015.

(51) Int. Cl.
*C10M 105/18* (2006.01)
*C07C 43/04* (2006.01)
(52) U.S. Cl.
CPC ........... *C10M 105/18* (2013.01); *C07C 43/04* (2013.01); *C07C 43/046* (2013.01);
(Continued)

(58) Field of Classification Search
CPC ............ C10M 105/18; C10M 2207/04; C10M 2207/0406; C10M 2203/1006;
(Continued)

(56) References Cited

U.S. PATENT DOCUMENTS 2,884,315 A * 4/1959 Barnum .................. C10L 1/023
44/448
7,622,431 B2 11/2009 Muir
(Continued)

FOREIGN PATENT DOCUMENTS

CN 102 558 465 B 3/2015
EP 1533362 A1 5/2005
(Continued)

OTHER PUBLICATIONS

American Petroleum Institute (API) 1509, "Annex E—API Base Oil Interchangeability Guidelines for Passenger Car Motor Oils and Diesel Engine Oils", Annex E (Dec. 2016 Version (Reissued Jan. 3, 2017).
(Continued)

*Primary Examiner* — James C Goloboy
(74) *Attorney, Agent, or Firm* — McDonnell Boehnen Hulbert & Berghoff LLP

(57) ABSTRACT

In some embodiments, a compound has the formula (I) where: $R_1$ and $R_2$ are alkyl or, together with the carbon atom to which they are attached, cycloalkyl; $R_3$, $R_4$ and $R_5$ are H or alkyl (formula II); $R_6$ is alkyl or where: $R_7$ and $R_8$ are H, alkyl or, together with the carbon atom to which they are attached, cycloalkyl; $R_9$ is H or alkyl; X is alkylene or is absent; and p is 0, 1, 2 or 3; and m and n are 0, 1, 2 or 3 provided that m is 0 when $R_4$ and $R_5$ are H. The compound is suitable for use as a base stock which provides low volatility for a given viscosity profile. The compound may be used in a lubricant composition for an internal combustion engine.

(Continued)

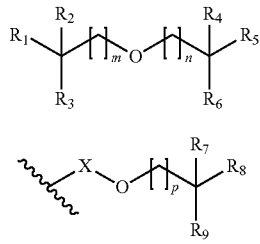

(I)

(II)

32 Claims, 4 Drawing Sheets

(52) U.S. Cl.
CPC ............. *C10M 2203/1006* (2013.01); *C10M 2203/1025* (2013.01); *C10M 2205/0285* (2013.01); *C10M 2207/0215* (2013.01); *C10M 2207/0225* (2013.01); *C10M 2207/0406* (2013.01); *C10N 2220/022* (2013.01); *C10N 2220/025* (2013.01); *C10N 2220/028* (2013.01); *C10N 2230/02* (2013.01); *C10N 2230/04* (2013.01); *C10N 2230/10* (2013.01); *C10N 2230/54* (2013.01); *C10N 2230/74* (2013.01); *C10N 2240/10* (2013.01)

(58) Field of Classification Search
CPC .. C10M 2203/1025; C10M 2205/0285; C10M 2207/0215; C10M 2207/0225; C10N 2240/10; C10N 2220/022; C10N 2220/025; C10N 2220/028; C10N 2230/02; C10N 2230/04; C10N 2230/10; C10N 2230/54; C07C 43/04
See application file for complete search history.

(56) References Cited

U.S. PATENT DOCUMENTS

| | | |
|---|---|---|
| 2005/0109130 A1 | 5/2005 | Ohi |
| 2005/0198894 A1 | 9/2005 | Migdal et al. |
| 2006/0045397 A1 | 3/2006 | Hirata |
| 2006/0090393 A1 | 5/2006 | Rowland et al. |
| 2007/0281873 A1* | 12/2007 | Okada ................. C10M 105/18 508/579 |
| 2013/0105740 A1 | 5/2013 | Wu et al. |
| 2013/0109604 A1 | 5/2013 | Patil |

FOREIGN PATENT DOCUMENTS

| | | | |
|---|---|---|---|
| EP | 1 577 371 A1 | 9/2005 | |
| EP | 1 752 515 A1 | 2/2007 | |
| EP | 2 924 003 A1 | 9/2015 | |
| EP | 2 937 918 A1 | 10/2015 | |
| JP | S4833037 A | 5/1973 | |
| JP | H0967289 A | 3/1997 | |
| JP | H10251181 A | 9/1998 | |
| JP | 2006064151 A | 3/2006 | |
| JP | 2006301309 A | 11/2006 | |
| JP | 2016011384 A | 1/2016 | |
| RU | 2068838 C1 | 11/1996 | |
| SU | 1549944 A1 | 3/1990 | |
| WO | WO-9411469 A1 * | 5/1994 | ............. C23F 11/00 |
| WO | 1999/021902 A1 | 5/1999 | |
| WO | 2003/099890 A2 | 12/2003 | |
| WO | 2006/099250 A1 | 9/2006 | |
| WO | 2014/207235 A1 | 6/2014 | |
| WO | WO-2014207235 A1 * | 12/2014 | .......... C10M 105/34 |
| WO | 2015/060985 A1 | 4/2015 | |

OTHER PUBLICATIONS

The International Search Report (ISR) for PCT/IB2016/000943 dated Aug. 31, 2016, pp. 1-4.
Written Opinion of the International Searching Authority for PCT/IB2016/000943 dated Aug. 31, 2016, pp. 1-7.
Gash, V.W., "Dienoalkyl ethers. General synthesis of the symmetrical ethers," Journal of Organic Chemistry 37(13): 2197-2201 (1972).

* cited by examiner

ETHER COMPOUNDS AND RELATED COMPOSITIONS

This application claims priority to International Patent Application No. PCT/IB2016/000943, filed Jun. 17, 2016, which claims priority to U.S. Provisional Application No. 62/181,536, filed Jun. 18, 2015.

The present invention relates, in part, to compounds which may be used as base stocks, in particular as base stocks which have a low volatility for a given viscosity profile, and which are suitable for use in a lubricant composition for an internal combustion engine. Base oils comprising said compounds and lubricant compositions comprising said base oils are also provided.

BACKGROUND

Lubricating compositions generally comprise a base oil of lubricating viscosity together with one or more additives to deliver properties including for example, reduced friction and wear, improved viscosity index, detergency, and resistance to oxidation and corrosion. A lubricant base oil may comprise one or more lubricating base stocks.

Lubricant base stocks used in automotive engine lubricants are generally obtained from petrochemical sources, for example they may be obtained as the higher boiling fractions isolated during the refining of crude oil or as the products of chemical reactions of feedstocks from petrochemical sources. Lubricant base stocks can also be made from Fischer-Tropsch wax.

Lubricant base stocks may be classified as Group I, II, III, IV and V base stocks according to API standard 1509, "ENGINE OIL LICENSING AND CERTIFICATION SYSTEM", 17$^{th}$ Edition, Annex E (October 2013 with Errata March 2015), as set out in Table 1.

TABLE 1

| Group | Saturated hydrocarbon content (% by weight) ASTM D2007 | Sulphur content (% by weight) ASTM D2622, D4294, D4927, D3120 or D1552 | Viscosity Index ASTM D2270 |
|---|---|---|---|
| I | <90 | and/or >0.03 | and ≥80 and <120 |
| II | ≥90 | and ≤0.03 | and ≥80 and <120 |
| III | ≥90 | and ≤0.03 | and ≥120 |
| IV | Polyalphaolefins | | |
| V | all base stocks not in Groups I, II, III or IV | | |

Group I base stocks are typically manufactured by known processes including, for example, solvent extraction and solvent dewaxing, or solvent extraction and catalytic dewaxing. Group II and Group III base stocks are typically manufactured by known processes including, for example, catalytic hydrogenation and/or catalytic hydrocracking, and catalytic hydroisomerisation. Group IV base stocks include for example, hydrogenated oligomers of alpha olefins.

A combination of properties is desirable in a base stock. In some instances, for example in passenger car engine oils, it may be desirable for a base stock to have a low viscosity profile, since this leads to improved fuel economy. In particular, it is desirable for base stocks to have a low kinematic viscosity as well as good low-temperature viscosity characteristics, for example a low pour point or low viscosity as measured using a mini-rotary viscometer (MRV). However, the general trend is for an improvement in the viscosity profile (i.e. a reduction in viscosity parameters) of a base oil to be accompanied by an undesirable increase in volatility.

Accordingly, there is a need in the art for a base stock having a desirable viscosity profile, including good low-temperature viscosity characteristics, but which also exhibits low volatility.

Problems may also be encountered when a base stock is incorporated into a lubricating composition and used in an engine. For instance, poor miscibility of a base stock with lubricant additives or other base stocks may lead to problems in the engine, for instance with piston cleanliness. Negative interactions between a base stock and oil seals that are found in engines may, in some cases, lead to loss of lubricant through failure of the oil seals. Base stocks may also undergo oxidative degradation at the high temperatures encountered in an engine. Base stocks containing polar groups such as ester or other groups may be particularly prone to at least some of these problems.

Accordingly, there is a need for a base stock having low volatility for a given viscosity profile, but which is also suitable for use, for example, in a lubricating composition for an internal combustion engine.

SUMMARY

A compound of formula (1) is provided:

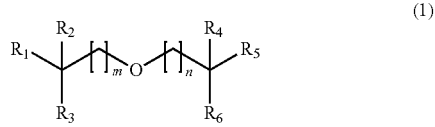

where: $R_1$ and $R_2$ are alkyl or, together with the carbon atom to which they are attached, cycloalkyl;
$R_3$, $R_4$ and $R_5$ are H or alkyl;
$R_6$ is alkyl or

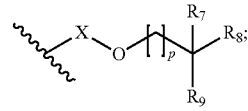

where: $R_7$ and $R_8$ are H, alkyl or, together with the carbon atom to which they are attached, cycloalkyl;
$R_9$ is H or alkyl;
X is alkylene or is absent; and
p is 0, 1, 2 or 3; and
m and n are 0, 1, 2 or 3 provided that m is 0 when $R_4$ and $R_5$ are H.

Compounds of formula (1) may be used as base stocks.
Also provided is a base oil comprising a compound of formula (1), as well as a lubricant composition comprising said base oil.

Also provided are methods of preparing base oils and lubricant compositions.

Also provided is a method for lubricating a surface using a lubricant composition, as well as the use of a lubricant composition for lubricating a surface.

Also provided are methods and uses of improving the oxidative stability performance, fuel economy performance and/or piston cleanliness performance of a lubricating composition, and of improving the fuel economy performance and/or piston cleanliness performance of an engine and/or vehicle.

DETAILED DESCRIPTION

Ether Base Stocks

A compound of formula (1) is provided:

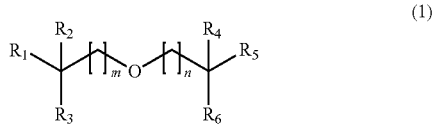

(1)

where: $R_1$ and $R_2$ are alkyl or, together with the carbon atom to which they are attached, cycloalkyl;
$R_3$, $R_4$ and $R_5$ are H or alkyl;
$R_6$ is alkyl or

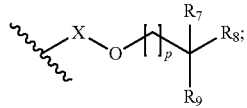

where: $R_7$ and $R_8$ are H, alkyl or, together with the carbon atom to which they are attached, cycloalkyl;
$R_9$ is H or alkyl;
X is alkylene or is absent; and
p is 0, 1, 2 or 3; and
m and n are 0, 1, 2 or 3 provided that m is 0 when $R_4$ and $R_5$ are H.

In some embodiments, $R_1$ and $R_2$ are $C_{1-15}$ alkyl or, together with the carbon atom to which they are attached, $C_{5-30}$ cycloalkyl, such as $C_{2-12}$ alkyl or, together with the carbon atom to which they are attached, $C_{5-25}$ cycloalkyl.

In some embodiments, $R_3$, $R_4$ and $R_5$ are H or $C_{1-15}$ alkyl, such as H or $C_{2-12}$ alkyl. Preferably, $R_5$ is H.

In some embodiments, $R_6$ is $C_{1-20}$ alkyl or

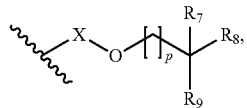

such as $C_{1-16}$ alkyl or

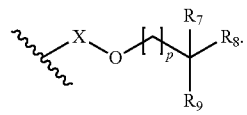

In some embodiments, $R_7$ and $R_8$ are H, $C_{1-20}$ alkyl or, together with the carbon atom to which they are attached, $C_{5-30}$ cycloalkyl, such as H, $C_{2-12}$ alkyl or, together with the carbon atom to which they are attached, $C_{5-25}$ cycloalkyl. Preferably, $R_7$ and $R_8$ are $C_{1-20}$ alkyl, such as $C_{2-12}$ alkyl.

In some embodiments, $R_9$ is H or $C_{1-20}$ alkyl, such as H or $C_{2-12}$ alkyl. Preferably, $R_9$ is H.

In some embodiments, X is $C_{1-20}$ alkylene, such as $C_{3-15}$ alkylene.

In some embodiments, p is 0, 1 or 2, such as 0 or 1.
In some embodiments, m and n are 0, 1 or 2, such as 0 or 1.

$R_1$ and $R_2$ are as described as alkyl or, together with the carbon atom to which they are attached, cycloalkyl. It will be understood that, where $R_1$ and $R_2$ are both alkyl groups, they may be the same as or different from one another. Similar considerations apply to other substituents which are defined as part of a group of substituents. Thus, the considerations apply, for example, to $R_3$, $R_4$ and $R_5$; to $R_7$ and $R_8$; and to the values taken by m and n. For instance, where $R_3$, $R_4$ and $R_5$ are described as being H or alkyl, it will be understood that each of $R_3$, $R_4$ and $R_5$ may be H, each of $R_3$, $R_4$ and $R_5$ may be alkyl, or a subset of $R_3$, $R_4$ and $R_5$ may be H and a subset alkyl. Where $R_3$, $R_4$ and $R_5$, or a subset thereof, are alkyl, each of $R_3$, $R_4$ and $R_5$ may be the same alkyl group or they may be different alkyl groups. In contrast, where $R_1$ (or any other notation) is used at a number of locations in a formula, it is used to denote the presence of the same group at each of these locations.

In each of the embodiments disclosed herein, the compounds may contain a total number of carbons atoms of from about 20 to about 50. For instance, the total number of carbons in the compounds may be from about 25 to about 45, such as from about 28 to about 40 or from about 30 to about 36.

The alkyl and alkylene groups mentioned herein, i.e. those that may be represented by $R_1$, $R_2$, $R_3$, $R_4$, $R_5$, $R_6$, $R_7$, $R_8$, $R_9$ and X, may be straight chain alkyl or alkylene groups, though they may also be branched. In some embodiments, each alkyl group and each alkylene group contains a single branch point or is a straight chain alkyl or alkylene group. The alkyl and alkylene groups are preferably straight chain alkyl or alkylene groups. It will be understood that, aside from alkyl branching (if present), the alkyl and alkylene groups are unsubstituted and so they do not contain any atoms other than carbon or hydrogen.

The cycloalkyl groups mentioned herein may contain a cyclopentyl, cyclohexyl or cycloheptyl group optionally having alkyl groups attached thereto.

The compounds of formula (1) may have a kinematic viscosity at 40° C. of less than about 25 cSt, such as less than about 20 cSt, or less than about 17 cSt. The compounds may have a kinematic viscosity at 100° C. of less than about 7 cSt, such as less than about 5 cSt, or less than about 4 cSt. The compounds may have a viscosity index of greater than about 100, such as greater than about 110, or greater than about 120. The kinematic viscosity at 40° C. and the kinematic viscosity at 100° C. may be measured according to ASTM D7279. The viscosity index may be measured according to ASTM D2270.

The compounds may have a Noack volatility of less than about 26%, such as less than about 20%, less than about 16%, or less than about 12% by weight. Noack volatility may be measured according to CEC-L-40-A-93.

The compounds may have a viscosity at 150° C. and a shear rate of $10^6$ $s^{-1}$ of no greater than 1.7 cP, such as no greater than 1.5 cP. This high temperature high shear viscosity may be measured according to CEC-L-36-A-90.

The compounds may be used to improve the oxidative stability, fuel economy performance and/or piston cleanliness performance of a lubricant composition, and/or the fuel economy performance and/or piston cleanliness performance of an internal combustion engine and/or a vehicle, such as an automotive vehicle associated with an internal combustion engine. Accordingly, there are provided methods of improving the fuel economy performance and/or piston cleanliness performance of a lubricant composition an internal combustion engine and/or a vehicle, such as an automotive vehicle associated with an internal combustion engine, comprising the step of providing or supplying to the lubricant composition, engine and/or vehicle at least one of the compounds.

The compounds may have a pour point of less than −10° C., such as less than about −25° C., or less than about −35° C. Pour point may be measured according to ASTM D5950.

The compounds may have a cold-crankcase simulator viscosity at −35° C. of less than about 1800 cP, such as less than about 1500 cP, or less than about 1200 cP, for example as measured according to ASTM D5293.

The compounds may have a DSC oxidation onset temperature of greater than about 165° C., such as greater than about 175° C., or greater than about 185° C., for example as measured according to ASTM E2009 (method B).

In particular embodiments, the compounds of formula (1) may have a kinematic viscosity at 100° C. of about 3 to about 4 cSt and a Noack volatility of less than about 20%, such as less than about 16%, or less than about 12%, by weight; or a kinematic viscosity at 100° C. of about 2 to about 3 cSt, and a Noack volatility of less than about 40%, such as less than about 30%, by weight.

The compounds of formula (1) are also particularly suited for blending into a lubricant composition. In particular, the compounds are miscible with conventional base stocks, including hydrocarbon base stocks, as well as with conventional lubricant additives. Moreover, the compounds may be used in a lubricant composition in a relatively high amount (for example, in an amount of greater than about 10% by weight, such as greater than about 20% by weight or greater than about 30% by weight) whilst meeting elastomer compatibility requirements for lubricant compositions.

The compounds of formula (1) may be prepared from a wide range of commercially available feedstocks.

In some embodiments, the compounds are prepared from bio-derived feedstocks. For instance, the compounds may contain greater than about 50%, such as greater than about 70%, or greater than about 90% by weight of biobased carbon. The biobased carbon content of the compounds may be measured according to ASTM D6866.

Guerbet-Derived Base Stocks

In preferred embodiments, the compounds of formula (1) are derived from β-alkylated alcohols. In these embodiments, the compound may have the formula (2):

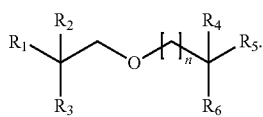
(2)

where: $R_1$ and $R_2$ are alkyl or, together with the carbon atom to which they are attached, cycloalkyl;
$R_3$ and $R_5$ are H or alkyl;
$R_4$ is alkyl;
$R_6$ is alkyl or

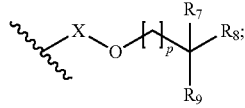

where: $R_7$ and $R_8$ are H, alkyl or, together with the carbon atom to which they are attached, cycloalkyl;
$R_9$ is H or alkyl;
X is alkylene or is absent; and
p is 0, 1, 2 or 3; and
n is 0, 1, 2 or 3.

In some embodiments, $R_1$ and $R_2$ are $C_{1-15}$ alkyl or, together with the carbon atom to which they are attached, $C_{5-30}$ cycloalkyl, such as $C_{2-12}$ alkyl or, together with the carbon atom to which they are attached, $C_{5-25}$ cycloalkyl. Preferably, $R_1$ and $R_2$ are $C_{1-15}$ alkyl, such as $C_{2-12}$ alkyl.

In some embodiments, $R_3$ and $R_5$ are H or $C_{1-15}$ alkyl, such as H or $C_{2-12}$ alkyl. Preferably, $R_3$ and $R_5$ are H.

In some embodiments, $R_4$ is $C_{1-15}$ alkyl, such as $C_{2-12}$ alkyl.

In some embodiments, $R_6$ is $C_{1-15}$ alkyl or

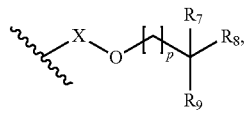

such as $C_{1-12}$ alkyl or

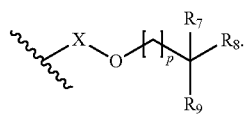

In some embodiments, $R_7$ and $R_8$ are H, $C_{1-20}$ alkyl or, together with the carbon atom to which they are attached, $C_{5-30}$ cycloalkyl, such as H, $C_{2-12}$ alkyl or, together with the carbon atom to which they are attached, $C_{5-25}$ cycloalkyl. Preferably, $R_7$ and $R_8$ are $C_{1-20}$ alkyl, such as $C_{2-12}$ alkyl.

In some embodiments, $R_9$ is H or $C_{1-20}$ alkyl, such as H or $C_{2-12}$ alkyl. Preferably, $R_9$ is H.

In some embodiments, X is $C_{1-20}$ alkylene, such as $C_{3-15}$ alkylene.

In some embodiments, p is 0, 1 or 2, such as 0 or 1.
In some embodiments, n is 0, 1 or 2, such as 0 or 1.

Where the compound is derived from a β-alkylated alcohol, it is preferably derived, at least in part, from a Guerbet alcohol. Compounds which are derived, at least in part, from Guerbet alcohols may have the formula (3):

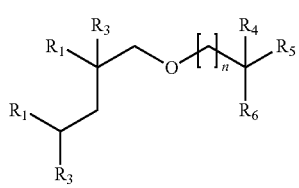
(3)

where: $R_1$ is alkyl;
$R_3$ and $R_5$ are H or alkyl;
$R_4$ is alkyl;
$R_6$ is alkyl or

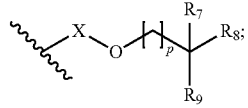

where: $R_7$ and $R_8$ are H, alkyl or, together with the carbon atom to which they are attached, cycloalkyl;
$R_9$ is H or alkyl;
X is alkylene or is absent; and
p is 0, 1, 2 or 3; and
n is 0, 1, 2 or 3.

In some embodiments, $R_1$ is $C_{1-12}$ alkyl, such as $C_{2-10}$ alkyl.

In some embodiments, $R_3$ is H or $C_{1-12}$ alkyl, such as H or $C_{2-10}$ alkyl. Preferably, $R_3$ is H.

In some embodiments, $R_4$ is $C_{1-15}$ alkyl, such as $C_{2-12}$ alkyl.

In some embodiments, $R_5$ is H or $C_{1-15}$ alkyl, such as H or $C_{2-12}$ alkyl. Preferably, $R_5$ is H.

In some embodiments, $R_6$ is $C_{1-15}$ alkyl or

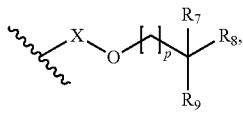

such as $C_{1-12}$ alkyl or

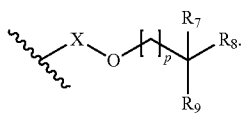

Preferably, $R_6$ is $C_{1-15}$ alkyl, such as $C_{1-12}$ alkyl.

In some embodiments, $R_7$ and $R_8$ are H, $C_{1-20}$ alkyl or, together with the carbon atom to which they are attached, $C_{5-30}$ cycloalkyl, such as H, $C_{2-12}$ alkyl or, together with the carbon atom to which they are attached, $C_{5-25}$ cycloalkyl. Preferably, $R_7$ and $R_8$ are $C_{1-20}$ alkyl, such as $C_{2-12}$ alkyl.

In some embodiments, $R_9$ is H or $C_{1-20}$ alkyl, such as H or $C_{2-12}$ alkyl. Preferably, $R_9$ is H.

In some embodiments, X is $C_{1-20}$ alkylene, such as $C_{3-15}$ alkylene.

In some embodiments, p is 0, 1 or 2, such as 0 or 1.
In some embodiments, n is 0, 1 or 2, such as 0 or 1.

One portion of the compound of formula (3) has a structure which may be derived from a Guerbet alcohol (i.e. the portion containing $R_1$ and $R_3$), whereas the other portion need not be derived from a Guerbet alcohol (i.e. the portion containing $R_4$, $R_5$ and $R_6$). However, in preferred embodiments, the compound may be derived from a combination of two Guerbet alcohols. A compound prepared in this way may have the formula (4):

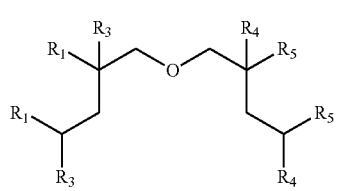

where: $R_1$ and $R_4$ are alkyl;
$R_3$ and $R_5$ are H or alkyl.
In some embodiments, $R_1$ and $R_4$ are $C_{1-12}$ alkyl, such as $C_{2-10}$ alkyl.

In some embodiments, $R_3$ and $R_5$ are H or $C_{1-12}$ alkyl, such as H or $C_{2-10}$ alkyl. Preferably, $R_3$ and $R_5$ are H.

In particular embodiments: $R_1$ is $C_{4-12}$ alkyl, such as $C_{6-10}$ alkyl;
$R_3$ is H;
$R_4$ is $C_{1-10}$ alkyl, such as $C_{2-8}$ alkyl; and
$R_5$ is H.

Two different Guerbet alcohols may be combined to form compounds of formula (4), in which case $R_1$ and $R_4$ may be different. Alternatively, $R_3$ and $R_5$ may be different. In some embodiments, $R_1$ and $R_4$ are different and $R_3$ and $R_5$ are also different.

However, in some embodiments, the compound may be derived from a reaction in which the same Guerbet alcohols are combined. A compound prepared in this way may have the formula (5):

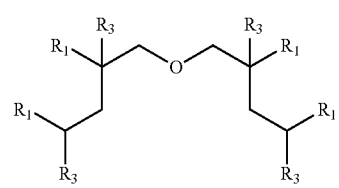

where: $R_1$ is alkyl; and
$R_3$ is H or alkyl.
In some embodiments, $R_1$ is $C_{1-10}$ alkyl, such as $C_{2-9}$ alkyl.

In some embodiments, $R_3$ is H or $C_{1-9}$ alkyl, such as H or $C_{2-8}$ alkyl. Preferably, $R_3$ is H.

In particular embodiments: $R_1$ is $C_{3-10}$ alkyl, such as $C_{4-8}$ alkyl; and
$R_3$ is H.

Compounds that are derived from Guerbet alcohols include compounds GE1-GE3, GE5, GE7-GE9, SE1, SE2 and TE1 as shown in Table 3.

Guerbet alcohols may be prepared, for example, by dimerising primary alcohols to form a β-alkylated alcohol product in a Guerbet reaction:

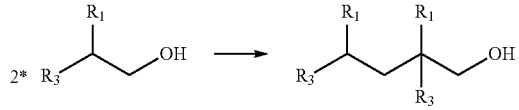

where $R_1$ and $R_3$ are as defined previously; and/or:

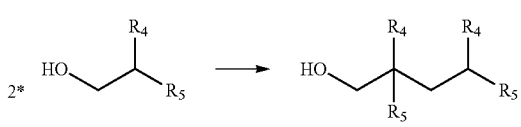

where $R_4$ and $R_5$ are as defined previously.

Guerbet reactions are well-known to the skilled person. The reactions are typically carried out at elevated temperatures in the presence of a catalyst.

The compound may be prepared from the Guerbet alcohol, for example, according to the following reaction:

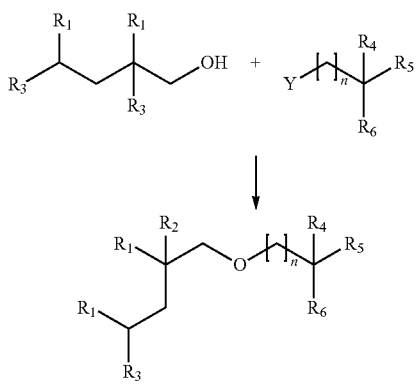

where: Y is a leaving group; and $R_1$, $R_3$, $R_4$, $R_5$, $R_6$ and n are as defined previously for the compound of formula (3).

Where two Guerbet alcohols are combined to form a compound, one of the Guerbet alcohols may first be modified so that it contains a leaving group, Y, and the compound then prepared:

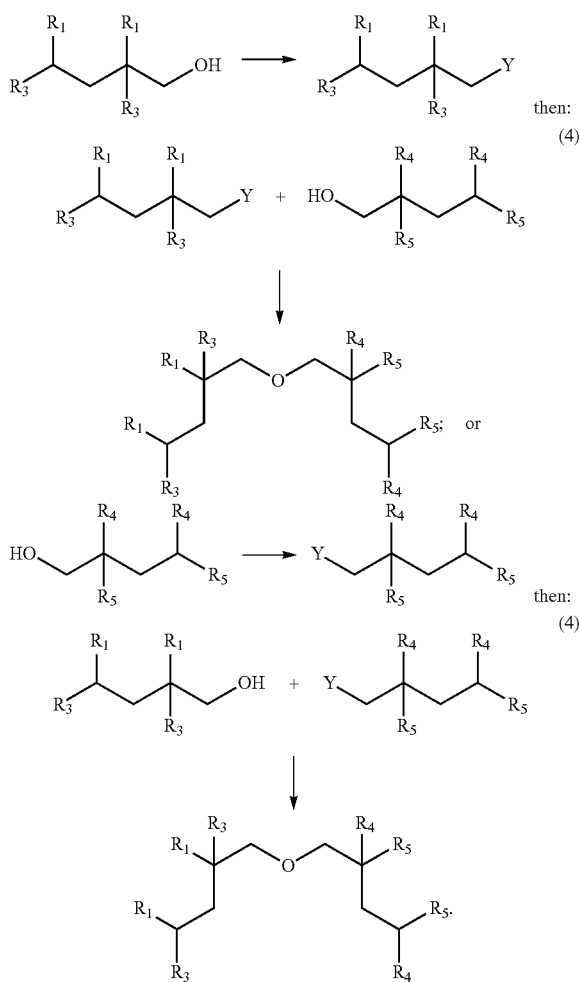

where: Y is a leaving group; and $R_1$, $R_3$, $R_4$ and $R_5$ are as defined previously for the compound of formula (4).

Where the same Guerbet alcohols are combined to form a compound, they may be combined, for example, according to the following reactions:

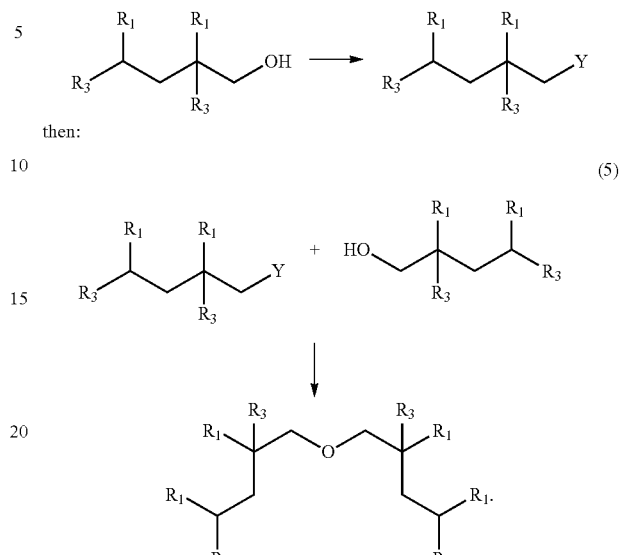

where: Y is a leaving group; and $R_1$ and $R_3$ are as defined previously for the compound of formula (5).

Methods and reaction conditions for modifying a Guerbet alcohol so that it contains a leaving group, Y, are known to the skilled person. For instance, a mesylate group may be introduced by reacting the Guerbet alcohol with mesyl chloride in the presence of triethylamine. A bromide group may be introduced by reacting the Guerbet alcohol with N-bromosuccinimide and triphenyl phosphine.

Methods and reaction conditions for carrying out etherification reactions are known to the skilled person. A base (for example potassium hydroxide or potassium tert-butoxide), a catalyst (for example Starks' catalyst: N-Methyl-N, N,N-trioctyloctan-1-ammonium chloride) or both may be used in the abovementioned compound forming reactions, i.e. the etherification reactions.

In the abovementioned compound forming reactions, Y may be any suitable leaving group, such as a halogen (for example bromine, chlorine or iodine) or a sulfonate ester (for example mesylate or tosylate).

Secondary and Tertiary Ether Base Stocks

In some preferred embodiments, the compounds of formula (1) are secondary or tertiary ether compounds. In these embodiments, the compound may have the formula (6):

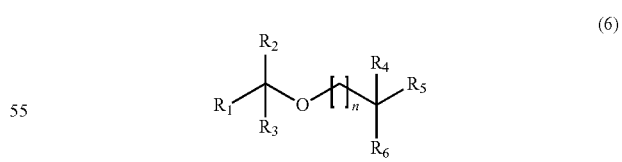

where: $R_1$ and $R_2$ are alkyl or, together with the carbon to which they are attached, cycloalkyl;

$R_3$, $R_4$ and $R_5$ are H or alkyl;

$R_6$ is alkyl or

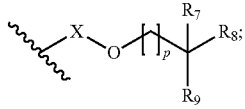

where: $R_7$ and $R_8$ are H, alkyl or, together with the carbon atom to which they are attached, cycloalkyl;
$R_9$ is H or alkyl;
X is alkylene or is absent; and
p is 0, 1, 2 or 3; and
n is 0, 1, 2 or 3.

In some embodiments, $R_1$ and $R_2$ are $C_{1-15}$ alkyl or, together with the carbon atom to which they are attached, $C_{5-30}$ cycloalkyl, such as $C_{2-12}$ alkyl or, together with the carbon atom to which they are attached, $C_{5-25}$ cycloalkyl. Preferably, $R_1$ and $R_2$ are $C_{1-15}$ alkyl, such as $C_{2-12}$ alkyl.

In some embodiments, $R_3$, $R_4$ and $R_5$ are H or $C_{1-15}$ alkyl, such as H or $C_{2-12}$ alkyl. Preferably, $R_5$ is H.

In some embodiments, $R_6$ is $C_{1-20}$ alkyl or

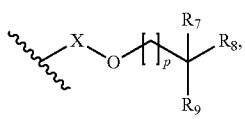

such as
$C_{1-16}$ alkyl or

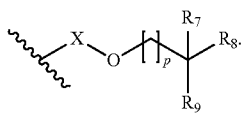

In some embodiments, $R_7$ and $R_8$ are H, $C_{1-20}$ alkyl or, together with the carbon atom to which they are attached, $C_{5-30}$ cycloalkyl, such as H, $C_{2-12}$ alkyl or, together with the carbon atom to which they are attached, $C_{5-25}$ cycloalkyl. Preferably, $R_7$ and $R_8$ are $C_{1-20}$ alkyl, such as $C_{2-12}$ alkyl.

In some embodiments, $R_9$ is H or $C_{1-20}$ alkyl, such as H or $C_{2-12}$ alkyl. Preferably, $R_9$ is H.

In some embodiments, X is $C_{1-20}$ alkylene, such as $C_{3-15}$ alkylene.

In some embodiments, p is 0, 1 or 2, such as 0 or 1.

In some embodiments, n is 0, 1 or 2, such as 0 or 1.

Secondary and tertiary ether compounds may have the formula (7):

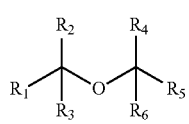

where: $R_1$ and $R_2$ are alkyl or, together with the carbon to which they are attached, cycloalkyl;
$R_3$, $R_4$ and $R_5$ are H or alkyl; and
$R_6$ is alkyl.

In some embodiments, $R_1$ and $R_2$ are $C_{1-15}$ alkyl or, together with the carbon to which they are attached, $C_{5-30}$ cycloalkyl, such as $C_{2-12}$ alkyl or, together with the carbon to which they are attached, $C_{5-25}$ cycloalkyl.

In some embodiments, $R_3$, $R_4$ and $R_5$ are H or $C_{1-15}$ alkyl, such as H or $C_{2-12}$ alkyl. Preferably, $R_5$ is H.

In some embodiments, $R_6$ is $C_{1-20}$ alkyl, such as $C_{1-16}$ alkyl.

The compounds may be secondary ether compounds of formula (8):

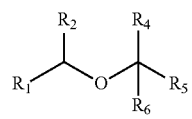

where: $R_1$ and $R_2$ are alkyl or, together with the carbon to which they are attached, cycloalkyl;
$R_4$ and $R_5$ are H or alkyl; and
$R_6$ is alkyl.

In some embodiments, $R_1$ and $R_2$ are $C_{1-15}$ alkyl, such as $C_{2-12}$ alkyl.

In other embodiments, the secondary ether may be obtained from a cyclic compound. In this case, $R_1$ and $R_2$, together with the carbon to which they are attached, form a cycloalkyl group, such as a $C_{5-30}$ cycloalkyl or a $C_{5-25}$ cycloalkyl. The cycloalkyl group may contain a cyclopentyl, cyclohexyl or cycloheptyl group optionally having one or more alkyl groups, such as $C_{1-12}$ alkyl or $C_{1-8}$ alkyl, attached thereto.

In some embodiments, $R_4$ and $R_5$ are H or $C_{1-15}$ alkyl, such as H or $C_{2-12}$ alkyl. Preferably, $R_5$ is H.

In some embodiments, $R_6$ is $C_{1-20}$ alkyl, such as $C_{1-16}$ alkyl.

In particular embodiments: $R_1$ and $R_2$ are $C_{3-12}$ alkyl, such as $C_{5-10}$ alkyl;
$R_4$ and $R_5$ are H; and
$R_6$ is $C_{4-20}$ alkyl, such as $C_{6-15}$ alkyl.

In other particular embodiments: $R_1$ and $R_2$ are $C_{3-12}$ alkyl, such as $C_{5-10}$ alkyl;
$R_4$ is $C_{3-12}$ alkyl, such as $C_{5-10}$ alkyl;
$R_5$ is H; and
$R_6$ is $C_{3-12}$ alkyl, such as $C_{5-10}$ alkyl.

The compounds may be tertiary ether compounds of formula (9):

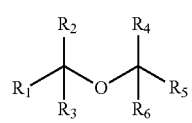

where: $R_1$ and $R_2$ are alkyl or, together with the carbon to which they are attached, cycloalkyl;
$R_3$ is alkyl;
$R_4$ and $R_5$ are H or alkyl; and
$R_6$ is alkyl.

In some embodiments, $R_1$ and $R_2$ are $C_{1-15}$ alkyl or, together with the carbon to which they are attached, $C_{5-30}$ cycloalkyl, such as $C_{2-12}$ alkyl or, together with the carbon to which they are attached, $C_{5-25}$ cycloalkyl. Preferably, $R_1$ and $R_2$ are $C_{1-15}$ alkyl, such as $C_{2-12}$ alkyl.

In some embodiments, $R_3$ is $C_{1-12}$ alkyl, such as $C_{1-10}$ alkyl.

In some embodiments, $R_4$ and $R_5$ are H or $C_{1-15}$ alkyl, such as H or $C_{2-12}$ alkyl.

In some embodiments, $R_6$ is $C_{1-20}$ alkyl, such as $C_{1-16}$ alkyl.

In particular embodiments: $R_1$ and $R_2$ are $C_{2-12}$ alkyl, such as $C_{4-10}$ alkyl;
$R_3$ is $C_{1-10}$ alkyl, such as $C_{1-8}$ alkyl;
$R_4$ and $R_5$ are H; and
$R_6$ is $C_{4-20}$ alkyl, such as $C_{6-15}$ alkyl.

In other particular embodiments: $R_1$, $R_2$ and $R_3$ are $C_{2-12}$ alkyl, such as $C_{4-10}$ alkyl;

$R_3$ is $C_{1-10}$ alkyl, such as $C_{1-8}$ alkyl;

$R_4$ is $C_{3-12}$ alkyl, such as $C_{5-10}$ alkyl;

$R_5$ is H; and $R_6$ is $C_{3-12}$ alkyl, such as $C_{5-10}$ alkyl.

Examples of secondary and tertiary ether compounds include SE1, SE2 and TE1 as shown in Table 3.

The secondary and tertiary ether compounds may be prepared according to the following reactions:

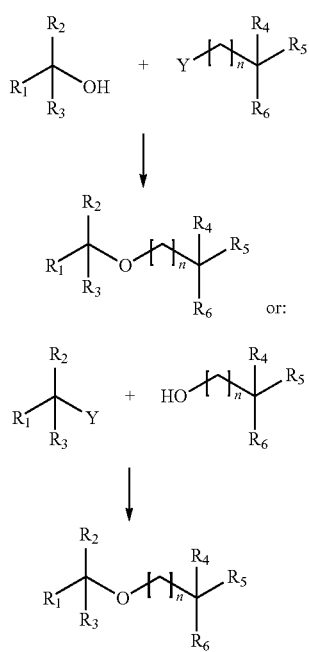

(6)

(6)

where: Y is a leaving group; and $R_1$, $R_2$, $R_3$, $R_4$, $R_5$, $R_6$ and n are as defined previously for the compound of formula (6).

Similarly:

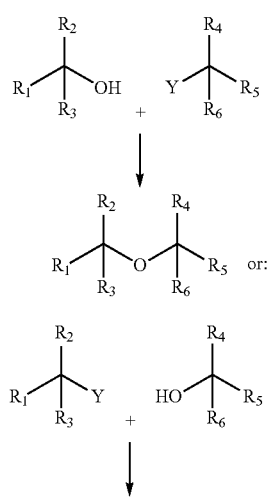

(7)

(7)

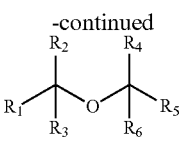

where: Y is a leaving group; and $R_1$, $R_2$, $R_3$, $R_4$, $R_5$ and $R_6$ are as defined previously for the compound of formula (7).

The skilled person will be aware of methods and reaction conditions for carrying out these etherification reactions. For instance, the reaction may be carried out in the presence of magnesium sulfate, sulfuric acid and dichloromethane.

Secondary and tertiary alcohol starting materials for use in etherification reactions will generally be commercially available, or they may be obtained from commercially available ketones.

The groups

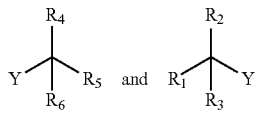

may be prepared by introducing a leaving group, Y, into the alcohol starting materials. Methods and reaction conditions for introducing the leaving group into alcohol are known to the skilled person.

In the abovementioned secondary and tertiary ether compound forming reactions, Y may be any suitable leaving group, such as a halogen (for example bromine, chlorine or iodine) or a sulfonate ester (for example mesylate or tosylate).

Secondary or Tertiary Ethers Derived from a Guerbet Alcohol

In some embodiments, the compound may comprise an ether which is derived on one side from a secondary or tertiary alcohol and is derived on the other side from a Guerbet alcohol. In these embodiments, the compound may have the formula (10):

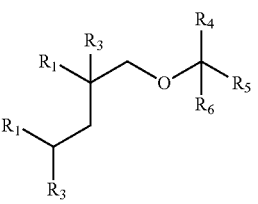

(10)

where: $R_1$ and $R_4$ are alkyl;

$R_3$ and $R_5$ are H or alkyl;

$R_6$ is alkyl or

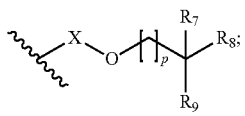

where: $R_7$ and $R_8$ are H, alkyl or, together with the carbon atom to which they are attached, cycloalkyl;

$R_9$ is H or alkyl;

X is alkylene or is absent; and and p is 0, 1, 2 or 3.

In some embodiments, $R_1$ is $C_{1-12}$ alkyl, such as $C_{2-10}$ alkyl.

In some embodiments, $R_3$ is H or $C_{1-12}$ alkyl, such as H or $C_{2-10}$ alkyl. Preferably, $R_3$ is H.

In some embodiments, $R_4$ is $C_{1-15}$ alkyl, such as $C_{2-12}$ alkyl.

In some embodiments, $R_5$ is H or $C_{1-15}$ alkyl, such as H or $C_{2-12}$ alkyl. Preferably, $R_5$ is H.

In some embodiments, $R_6$ is $C_{1-15}$ alkyl or

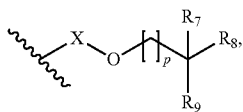

such as $C_{1-12}$ alkyl or

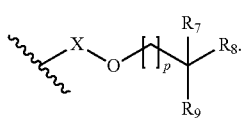

In some embodiments, $R_7$ and $R_8$ are H, $C_{1-20}$ alkyl or, together with the carbon atom to which they are attached, $C_{5-30}$ cycloalkyl, such as H, $C_{2-12}$ alkyl or, together with the carbon atom to which they are attached, $C_{5-25}$ cycloalkyl. Preferably, $R_7$ and $R_8$ are $C_{1-20}$ alkyl, such as $C_{2-12}$ alkyl.

In some embodiments, $R_9$ is H or $C_{1-20}$ alkyl, such as H or $C_{2-12}$ alkyl. Preferably, $R_9$ is H.

In some embodiments, X is $C_{1-20}$ alkylene, such as $C_{3-15}$ alkylene.

In some embodiments, p is 0, 1 or 2, such as 0 or 1.

Examples of secondary and tertiary ether compounds derived from a Guerbet-alcohol include compounds SE1, SE2 and TE1 as shown in Table 3.

Di-Ether Base Stocks

It is generally preferred that the compounds of formula (1) are monoethers. However, in some embodiments, the compound is a diether compound. Such compounds may have the formula (11):

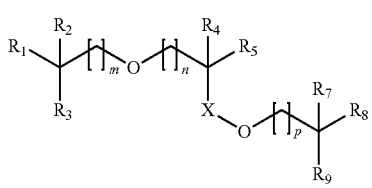

where: $R_1$ and $R_2$ are alkyl or, together with the carbon atom to which they are attached, cycloalkyl;
$R_3$, $R_4$ and $R_5$ are H or alkyl;
$R_7$ and $R_8$ are H, alkyl or, together with the carbon atom to which they are attached, cycloalkyl;
$R_9$ is H or alkyl;
X is alkylene or is absent;
p is 0, 1, 2 or 3; and
m and n are 0, 1, 2 or 3.

In some embodiments, $R_1$ and $R_2$ are $C_{1-15}$ alkyl or, together with the carbon to which they are attached, $C_{5-30}$ cycloalkyl, such as $C_{2-12}$ alkyl or, together with the carbon atom to which they are attached, $C_{5-25}$ cycloalkyl. Preferably, $R_1$ and $R_2$ are $C_{1-15}$ alkyl, such as $C_{2-12}$ alkyl.

In some embodiments, $R_3$, $R_4$ and $R_5$ are H or $C_{1-15}$ alkyl, such as H or $C_{2-12}$ alkyl. Preferably, $R_3$ and $R_5$ are H.

In some embodiments, $R_7$ and $R_8$ are H, $C_{1-20}$ alkyl or, together with the carbon atom to which they are attached, $C_{5-30}$ cycloalkyl, such as H, $C_{2-12}$ alkyl or, together with the carbon atom to which they are attached, $C_{5-25}$ cycloalkyl. Preferably, $R_7$ and $R_8$ are $C_{1-20}$ alkyl, such as $C_{2-12}$ alkyl.

In some embodiments, $R_9$ is H or $C_{1-20}$ alkyl, such as H or $C_{2-12}$ alkyl. Preferably, $R_9$ is H.

In some embodiments, X is $C_{1-20}$ alkylene, such as $C_{3-15}$ alkylene.

In some embodiments, p is 0, 1 or 2, such as 0 or 1.

In some embodiments, m and n are 0, 1 or 2, such as 0 or 1.

In some embodiments, the diether compound may contain two ether groups, at least one of which is derived from a β-alkylated alcohol. In such embodiments, the compound may have the formula (12):

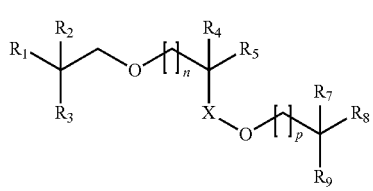

where: $R_1$ and $R_2$ are alkyl or, together with the carbon atom to which they are attached, cycloalkyl;
$R_3$, $R_4$ and $R_5$ are H or alkyl;
$R_7$ and $R_8$ are H, alkyl or, together with the carbon atom to which they are attached, cycloalkyl;
$R_9$ is H or alkyl;
X is alkylene or is absent;
p is 0, 1, 2 or 3; and
n is 0, 1, 2 or 3.

In some embodiments, $R_1$ and $R_2$ are $C_{1-15}$ alkyl or, together with the carbon atom to which they are attached, $C_{5-30}$ cycloalkyl, such as $C_{2-12}$ alkyl or, together with the carbon atom to which they are attached, $C_{5-25}$ cycloalkyl. Preferably, $R_1$ and $R_2$ are $C_{1-15}$ alkyl, such as $C_{2-12}$ alkyl.

In some embodiments, $R_3$, $R_4$ and $R_5$ are H or $C_{1-15}$ alkyl, such as H or $C_{2-12}$ alkyl. Preferably, $R_3$ and $R_5$ are H. Preferably, $R_4$ is $C_{1-15}$ alkyl, such as $C_{2-12}$ alkyl In some embodiments, $R_7$ and $R_8$ are H, $C_{1-20}$ alkyl or, together with the carbon atom to which they are attached, $C_{5-30}$ cycloalkyl, such as H, $C_{2-12}$ alkyl or, together with the carbon atom to which they are attached, $C_{5-25}$ cycloalkyl. Preferably, $R_7$ and $R_8$ are $C_{1-20}$ alkyl, such as $C_{2-12}$ alkyl.

In some embodiments, $R_9$ is H or $C_{1-20}$ alkyl, such as H or $C_{2-12}$ alkyl. Preferably, $R_9$ is H.

In some embodiments, X is $C_{1-20}$ alkylene, such as $C_{3-15}$ alkylene.

In some embodiments, p is 0, 1 or 2, such as 0 or 1.

In some embodiments, n is 0, 1 or 2, such as 0 or 1.

Base Oils and Lubricant Compositions

The compounds of formula (1) may be used as part of a base oil.

The base oils may contain an amount of compound of formula (1) which is sufficient to impart beneficial properties of the compound onto the base oil.

In some embodiments, the base oil comprises greater than about 5%, such as greater than about 25%, or greater than about 40% by weight of compound of formula (1). The base oil may comprise up to about 100%, such as up to about 90% of compound of formula (1). The compound of formula (1) in the base oil may be composed of a single compound or a combination of compounds of formula (1).

The remainder of the base oil may be made up with base stocks which are not compounds of formula (1). Base stocks other than those of formula (1) which are suitable for use in the base oil include non-aqueous base stocks, such as Group I, Group II, Group III, Group IV and Group V base stocks. The remainder of the base oil may comprise a single base stock or a combination of base stocks other than those of formula (1).

The base oils may be used as part of a lubricant composition.

The lubricant compositions may contain an amount of base oil which is sufficient to impart beneficial properties of the compound of formula (1) onto the lubricating composition.

In some embodiments, the lubricant composition comprises greater than about 50%, such as greater than about 65%, or greater than about 80% by weight of base oil. The base oil may be composed of a single base oil or a combination of base oils comprising compound of formula (1).

The lubricant composition may also comprise lubricant additives. The lubricant composition may comprise a single lubricant additive, though it will typically comprise a combination of lubricant additives. The lubricant additives will typically be present in the lubricant composition in an amount of from about 5% to about 40% by weight, such as about 10% to about 30% by weight.

Suitable lubricant additives include detergents (including metallic and non-metallic detergents), friction modifiers, dispersants (including metallic and non-metallic dispersants), viscosity modifiers, dispersant viscosity modifiers, viscosity index improvers, pour point depressants, anti-wear additives, rust inhibitors, corrosion inhibitors, antioxidants (sometimes also called oxidation inhibitors), anti-foams (sometimes also called anti-foaming agents), seal swell agents (sometimes also called seal compatibility agents), extreme pressure additives (including metallic, non-metallic, phosphorus containing, non-phosphorus containing, sulphur containing and non-sulphur containing extreme pressure additives), surfactants, demulsifiers, anti-seizure agents, wax modifiers, lubricity agents, anti-staining agents, chromophoric agents, metal deactivators, and mixtures of two or more thereof.

In some embodiments, the lubricant composition comprises a detergent. Examples of detergents include ashless detergents (that is, non-metal containing detergents) and metal-containing detergents. Suitable non-metallic detergents are described for example in U.S. Pat. No. 7,622,431. Metal-containing detergents comprise at least one metal salt of at least one organic acid, which is called soap or surfactant. Suitable organic acids include for example, sulphonic acids, phenols (suitably sulphurised and including for example, phenols with more than one hydroxyl group, phenols with fused aromatic rings, phenols which have been modified for example, alkylene bridged phenols, and Mannich base-condensed phenols and saligenin-type phenols, produced for example by reaction of phenol and an aldehyde under basic conditions) and sulphurised derivatives thereof, and carboxylic acids including for example, aromatic carboxylic acids (for example hydrocarbyl-substituted salicylic acids and derivatives thereof, for example hydrocarbyl substituted salicylic acids and sulphurised derivatives thereof).

In some embodiments, the lubricant composition comprises a friction modifier. Suitable friction modifiers include for example, ash-producing additives and ashless additives. Examples of suitable friction modifiers include fatty acid derivatives including for example, fatty acid esters, amides, amines, and ethoxylated amines. Examples of suitable ester friction modifiers include esters of glycerol for example, mono-, di-, and tri-oleates, mono-palmitates and mono-myristates. A particularly suitable fatty acid ester friction modifier is glycerol monooleate. Examples of suitable friction modifiers also include molybdenum compounds for example, organo molybdenum compounds, molybdenum dialkyldithiocarbamates, molybdenum dialkylthiophosphates, molybdenum disulphide, tri-molybdenum cluster dialkyldithiocarbamates, non-sulphur molybdenum compounds and the like. Suitable molybdenum-containing compounds are described for example, in EP 1533362 A1 for example in paragraphs [0101] to [0117].

In some embodiments, the lubricant composition comprises a dispersant. Examples of suitable ashless dispersants include oil soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons containing polyamine moieties attached directly thereto; Mannich condensation products formed by condensing a long chain substituted phenol with formaldehyde and polyalkylene polyamine; Koch reaction products and the like.

In some embodiments, the lubricant composition comprises a dispersant viscosity modifier. Examples of suitable dispersant viscosity modifiers and methods of making them are described in WO 99/21902, WO 2003/099890 and WO 2006/099250.

In some embodiments, the lubricant composition comprises a viscosity index improver. Examples of suitable viscosity modifiers include high molecular weight hydrocarbon polymers (for example polyisobutylene, copolymers of ethylene and propylene and higher alpha-olefins); polyesters (for example polymethacrylates); hydrogenated poly (styrene-co-butadiene or isoprene) polymers and modifications (for example star polymers); and esterified poly (styrene-co-maleic anhydride) polymers. Oil-soluble viscosity modifying polymers generally exhibit number average molecular weights of at least about 15000 to about 1000000, such as about 20000 to about 600000 as determined by gel permeation chromatography or light scattering methods.

In some embodiments, the lubricant composition comprises a pour point depressant. Examples of suitable pour point depressants include $C_8$ to $C_{18}$ dialkyl fumarate/vinyl acetate copolymers, methacrylates, polyacrylates, polyarylamides, polymethacrylates, polyalkyl methacrylates, vinyl fumarates, styrene esters, condensation products of haloparaffin waxes and aromatic compounds, vinyl carboxylate polymers, terpolymers of dialkyfumarates, vinyl esters of fatty acids and allyl vinyl ethers, wax naphthalene and the like. In at least some examples, the at least one lubricant additive includes at least one anti-wear additive. Examples of suitable anti-wear additives include non-phosphorus containing additives for example, sulphurised olefins. Examples of suitable anti-wear additives also include phosphorus-containing anti-wear additives. Examples of suitable ashless phosphorus-containing anti-wear additives include trilauryl phosphite and triphenylphosphorothionate and those disclosed in paragraph [0036] of US 2005/0198894. Examples of suitable ash-forming, phosphorus-containing anti-wear additives include dihydrocarbyl dithiophosphate metal salts. Examples of suitable metals of the dihydrocarbyl dithiophosphate metal salts include alkali and alkaline earth metals, aluminium, lead, tin, molybdenum, manganese, nickel, copper and zinc. Particularly suitable dihydrocarbyl dithiophosphate metal salts are zinc dihydrocarbyl dithiophosphates (ZDDP).

In some embodiments, the lubricant composition comprises a rust inhibitor. Examples of suitable rust inhibitors include non-ionic polyoxyalkylene polyols and esters thereof, polyoxyalkylene phenols, polyoxyalkylene polyols, anionic alky sulphonic acids, zinc dithiophosphates, metal phenolates, basic metal sulphonates, fatty acids and amines.

In some embodiments, the lubricant composition comprises a corrosion inhibitor. Examples of suitable corrosion inhibitors include phosphosulphurised hydrocarbons and the products obtained by the reaction of phosphosulphurised hydrocarbon with an alkaline earth metal oxide or hydroxide, non-ionic polyoxyalkylene polyols and esters thereof, polyoxyalkylene phenols, thiadiazoles, triazoles and anionic alkyl sulphonic acids. Examples of suitable epoxidised ester corrosion inhibitors are described in US 2006/0090393.

In some embodiments, the lubricant composition comprises an antioxidant. Examples of suitable antioxidants include alkylated diphenylamines, N-alkylated phenylenediamines, phenyl-a-naphthylamine, alkylated phenyl-a-naphthylamines, dimethylquinolines, trimethyldihydroquinolines and oligomeric compositions derived therefrom, hindered phenolics (including ashless (metal-free) phenolic compounds and neutral and basic metal salts of certain phenolic compounds), aromatic amines (including alkylated and non-alkylated aromatic amines), sulphurised alkyl phenols and alkali and alkaline earth metal salts thereof, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds (for example, copper dihydrocarbyl thio- or thio-phosphate, copper salts of a synthetic or natural carboxylic acids, for example a $C_8$ to $C_{18}$ fatty acid, an unsaturated acid or a branched carboxylic acid, for example basic, neutral or acidic Cu(I) and/or Cu(II) salts derived from alkenyl succinic acids or anhydrides), alkaline earth metal salts of alkylphenolthioesters, suitably containing $C_5$ to $C_{12}$ alkyl side chains, calcium nonylphenol sulphide, barium t-octylphenyl sulphide, dioctylphenylamine, phosphosulphised or sulphurised hydrocarbons, oil soluble phenates, oil soluble sulphurised phenates, calcium dodecylphenol sulphide, phosphosulphurised hydrocarbons, sulphurised hydrocarbons, phosphorus esters, low sulphur peroxide decomposers and the like.

In some embodiments, the lubricant composition comprises an antifoam agent. Examples of suitable anti-foam agents include silicones, organic polymers, siloxanes (including poly siloxanes and (poly) dimethyl siloxanes, phenyl methyl siloxanes), acrylates and the like.

In some embodiments, the lubricant composition comprises a seal swell agent. Examples of suitable seal swell agents include long chain organic acids, organic phosphates, aromatic esters, aromatic hydrocarbons, esters (for example butylbenzyl phthalate) and polybutenyl succinic anhydride.

The lubricant composition may comprise lubricant additives in the amounts shown in Table 2.

TABLE 2

| | Lubricant composition | |
|---|---|---|
| Additive type | Suitable amount (actives) if present by weight | Preferred amount (actives) if present by weight |
| Phosphorus-containing anti-wear additives | Corresponding to about 10 to about 6000 ppm P | Corresponding to about 10 to about 1000 ppm P |
| Molybdenum-containing anti-wear additives | Corresponding to about 10 to about 1000 ppm Mo | Corresponding to about 40 to about 600 ppm Mo |
| Boron-containing anti-wear additives | Corresponding to about 10 to about 500 ppm B | Corresponding to about 50 to about 100 ppm B |
| Friction modifiers | About 0.01 to about 5% | About 0.01 to about 1.5% |
| Molybdenum-containing friction modifiers | Corresponding to about 10 to about 1000 ppm Mo | Corresponding to about 400 to about 600 ppm Mo |
| Dispersants | About 0.1 to about 20% | About 0.1 to about 8% |
| Detergents | About 0.01 to about 6% | About 0.01 to about 4% |
| Viscosity index improvers | About 0.01 to about 20% | About 0.01 to about 15% |
| Pour point depressants | About 0.01 to about 5% | About 0.01 to about 1.5% |
| Corrosion and/or rust inhibitors | About 0.01 to about 5% | About 0.01 to about 1.5% |
| Anti-oxidants | About 0.01 to about 10% | About 0.5 to 5 about % |
| Antifoams containing silicon | Corresponding to about 1 to about 20 ppm Si | Corresponding to about 1 to about 10 ppm Si |

The lubricant compositions may have a kinematic viscosity at 40° C. of less than about 60 cSt, such as less than about 55 cSt, or less than about 50 cSt. The lubricant compositions may have a kinematic viscosity at 100° C. of less than about 12 cSt, such as less than about 10 cSt, or less than about 9.5 cSt. The lubricant compositions may have a viscosity index of greater than about 100, such as greater than about 110, or greater than about 120. The kinematic viscosity at 40° C. and the kinematic viscosity at 100° C. may be measured according to ASTM D445. The viscosity index may be calculated according to ASTM D2270.

The lubricant compositions may have a Noack volatility of less than about 25%, such as less than about 15%, or less than about 10% by weight. Noack volatility may be measured according to CEC-L-40-A-93.

The lubricant compositions may have a viscosity at 150° C. and a shear rate of $10^6$ s$^{-1}$ of no greater than 3 cP, such as no greater than 2.8 cP. This high temperature high shear viscosity may be measured according to CEC-L-36-A-90.

The lubricant composition may have at least one of:
an oxidative stability performance on a CEC-L-088-02 test indicated by an absolute viscosity increase at 40° C. of no more than 45 cSt, such as no more than 35 cSt or no more than 25 cSt; a fuel economy performance on a CEC-L-054-

96 test of at least 2.5%, such as at least 3%; and a piston cleanliness performance on a CEC-L-088-02 test indicated by an overall piston merit of at least 8.5, such as 9.

The lubricant compositions may have a cold-crankcase simulator performance at −30° C. of less than about 3000, such as less than about 2800, or less than about 2750, for example as measured according to ASTM D5293.

Preferred lubricant compositions meet the requirements set out in SAE J300.

The lubricant compositions may be used in a method of lubricating a surface.

Suitable surfaces include those in power transmission systems for example drive lines and gear boxes for example for vehicles including for example passenger vehicles and heavy duty vehicles; and those in internal combustion engines, for example the crankcases of internal combustion engines. Suitable surfaces also include those in turbine bearings for example in water turbine bearings.

Suitable internal combustion engines include, for example, engines used in automotive applications, engines used in marine applications and engines used in land-based power generation plants. The lubricant compositions are particularly suited to use in an automotive internal combustion engine.

The lubricant compositions may be used to improve the fuel economy and/or piston cleanliness performance of an internal combustion engine and/or a vehicle, such as an automotive vehicle associated with an internal combustion engine. Accordingly, there are provided methods of improving the fuel economy and/or piston cleanliness performance of an internal combustion engine and/or a vehicle, such as an automotive vehicle associated with an internal combustion engine, comprising the step of providing or supplying to the engine and/or vehicle at least one of the lubricant compositions.

The invention will now be described with reference to the accompanying figures and examples, which are not limiting in nature, in which.

Figure 4A:
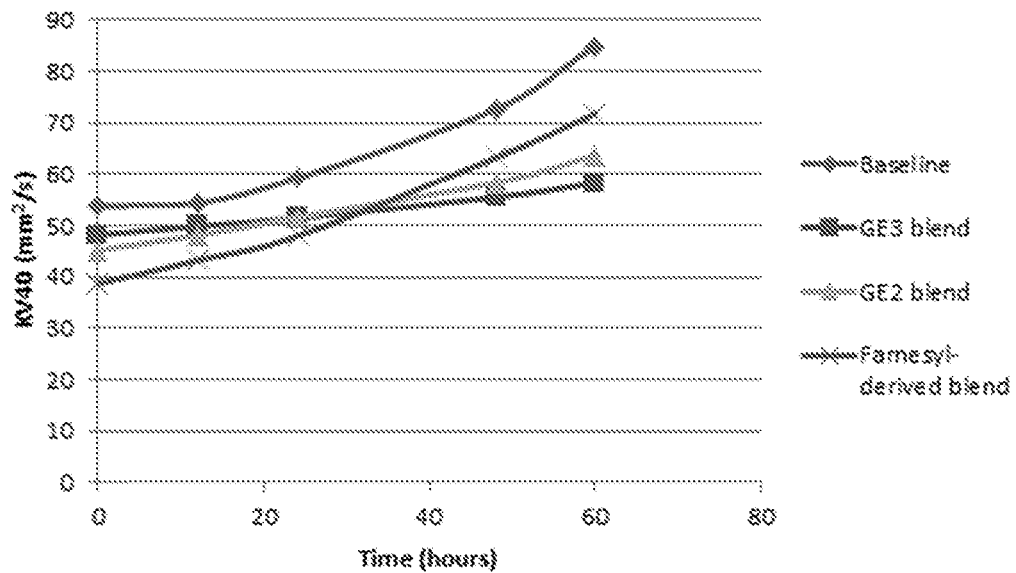
FIG. 4a is a graph of kinematic viscosity at 40° C. against time of lubricant compositions containing compounds of formula (1), a conventional hydrocarbon base stock and a farnesene-derived ether base stock during a TU-5 JP engine test.
Figure 4B:
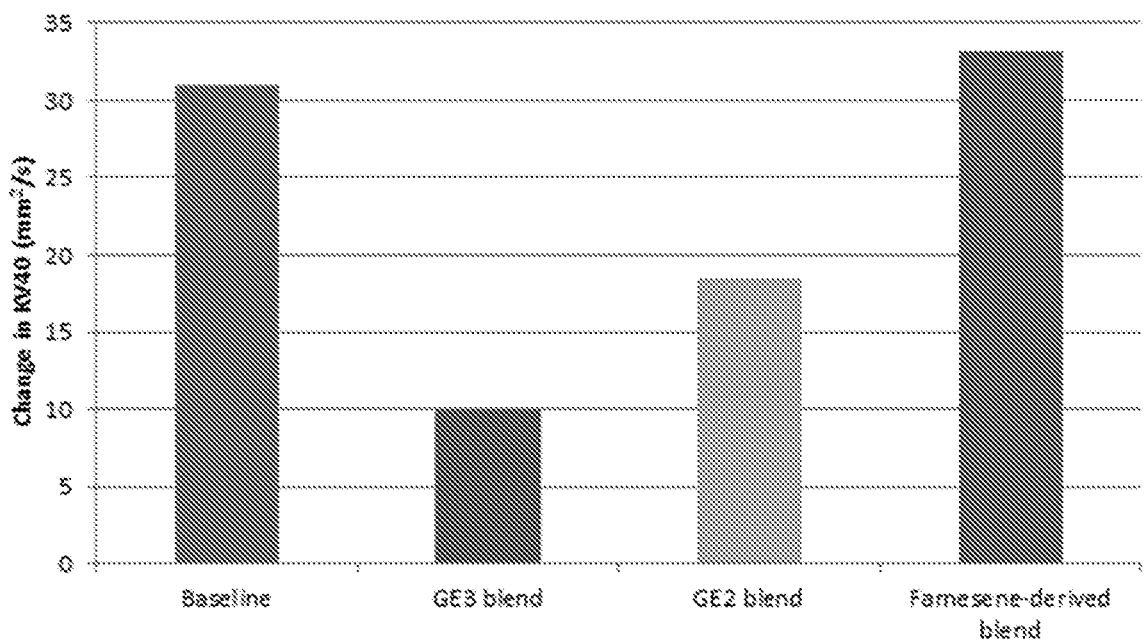
Figure 5:
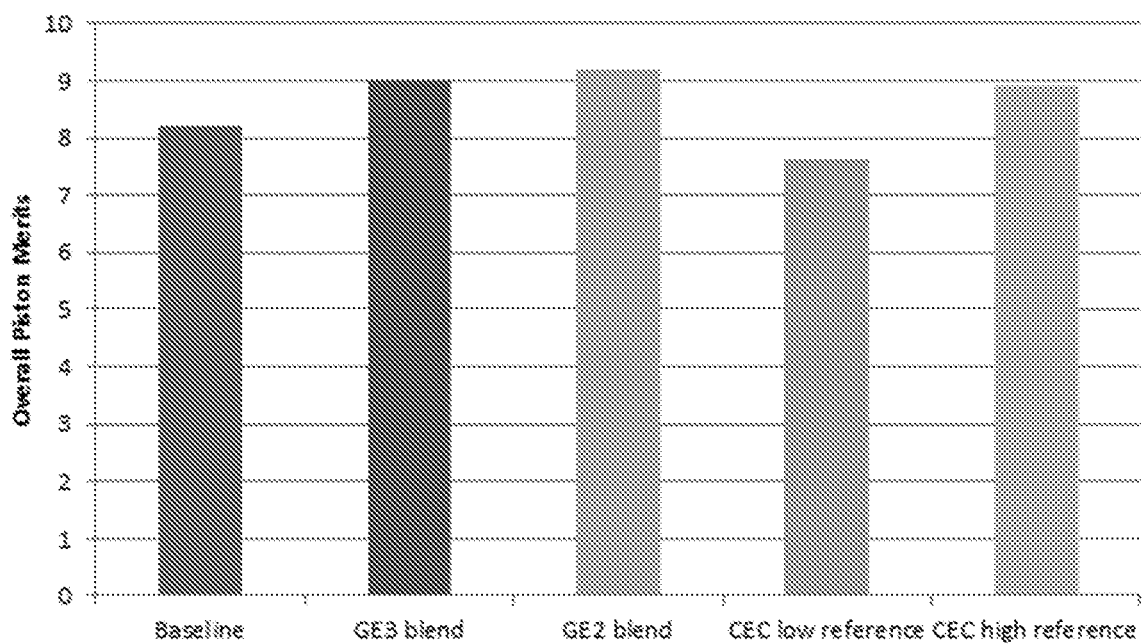

FIG. 4b is a graph of absolute change in kinematic viscosity at 40° C. of lubricant compositions containing compounds of formula (1), a conventional hydrocarbon base stock and a farnesene-derived ether base stock during a TU-5 JP engine test; and FIG. 5 is a graph of overall piston merit performance of lubricant compositions containing compounds of formula (1) and a conventional hydrocarbon base stock during a TU-5 JP engine test.

EXAMPLES

Example 1—Properties of Ether Base Stocks

Guerbet-derived base stocks GE1-GE3, GE5 and GE7-GE9, secondary ether base stocks SE1 and SE2, and tertiary ether base stock TE1 of formula (1) were prepared. Two further Guerbet-derived base stocks, GE4 and GE6, and an experimental group V base stock of the type previously described in WO 2014/207235, i.e. a farnesene-derived ether base stock, were also prepared. The structure of these compounds is shown in Table 3.

TABLE 3

| | Molecular Weight | Chemical Formula | Structure |
|---|---|---|---|
| GE1 | 466.87 | $C_{32}H_{66}O$ | 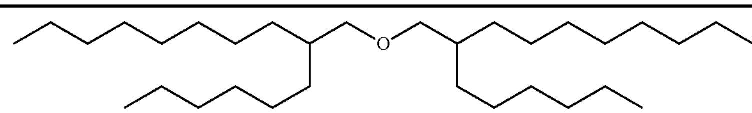 |
| GE2 | 466.87 | $C_{32}H_{66}O$ | 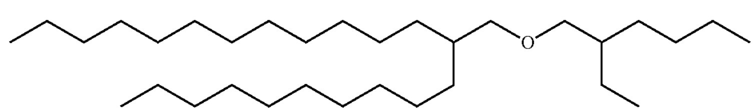 [SMILES: CCCCCCCCCCCCC(CCCCCCCCCC)COCC(CC)CCCC] |
| GE3 | 522.97 | $C_{36}H_{74}O$ | 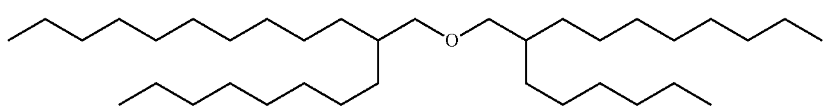 [SMILES: CCCCCCCCCCC(CCCCCCCC)COCC(CCCCCC)CCCCCCCC] |
| GE4 | 466.87 | $C_{32}H_{66}O$ | 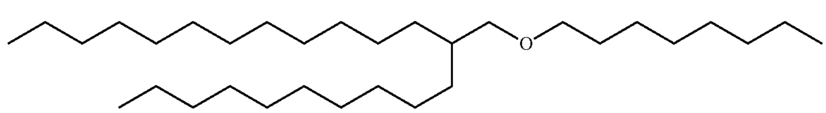 [SMILES: CCCCCCCCCCCCC(CCCCCCCCCC)COCCCCCCCC] |
| GE5 | 410.76 | $C_{28}H_{58}O$ | 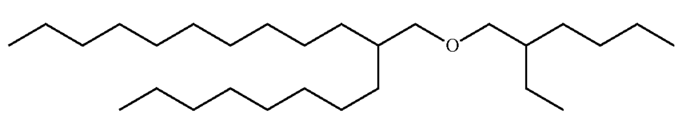 [SMILES: CCCCCCCCCCC(CCCCCCCC)COCC(CC)CCCC] |

TABLE 3-continued

| | Molecular Weight | Chemical Formula | Structure |
|---|---|---|---|
| GE6 | 466.87 | $C_{32}H_{66}O$ | 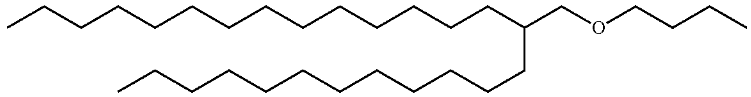 [SMILES: CCCCCCCCCCCCCCC(CCCCCCCCCCCC)COCCCC] |
| GE7 | 522.57 | $C_{36}H_{74}O$ | 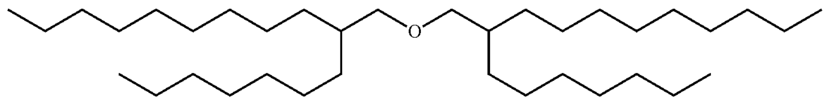 [SMILES: CCCCCCCCCC(CCCCCCC)COCC(CCCCCCC)CCCCCCCCC] |
| GE8 | 382.42 | $C_{26}H_{54}O$ | 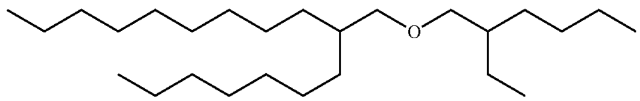 [SMILES: CCCCCCCCCC(CCCCCCC)COCC(CC)CCCC] |
| GE9 | 466.51 | $C_{32}H_{66}O$ | 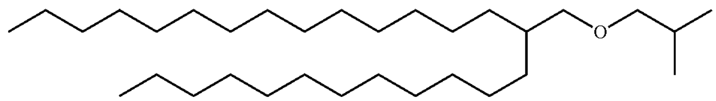 [SMILES: CCCCCCCCCCCCCCC(CCCCCCCCCCCC)COCC(C)C] |
| GE10 | 410.76 | $C_{28}H_{58}O$ | 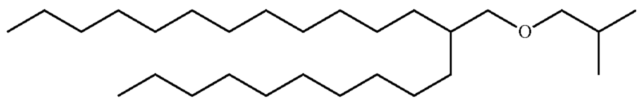 [SMILES: CCCCCCCCCCCCC(CCCCCCCCCC)COCC(C)C] |
| GE12 | 382.71 | $C_{26}H_{54}O$ | 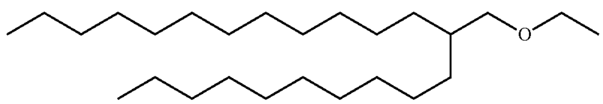 [SMILES: CCCCCCCCCCCCC(CCCCCCCCCC)COCC] |
| GE14 | 410.76 | $C_{28}H_{58}O$ | 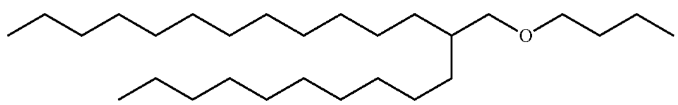 [SMILES: CCCCCCCCCCCCC(CCCCCCCCCC)COCCCC] |
| GE15 | 354.65 | $C_{24}H_{50}O$ | 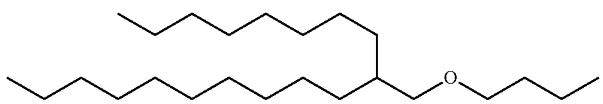 [SMILES: CCCCCCCCCCC(CCCCCCCC)COCCCC] |
| GE16 | 424.79 | $C_{29}H_{60}O$ | 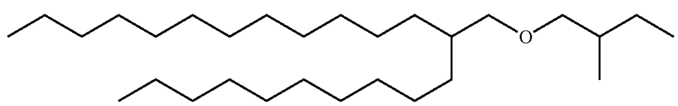 [SMILES: CCCCCCCCCCCCC(CCCCCCCCCC)COCC(C)CC] |
| GE18 | 438.81 | $C_{30}H_{62}O$ | 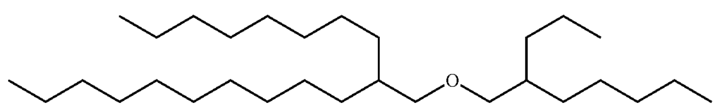 [SMILES: CCCCCCCCCCC(CCCCCCCC)COCC(CCC)CCCCC] |
| GE20 | 354.65 | $C_{24}H_{50}O$ | 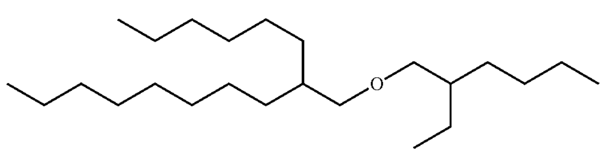 [SMILES: CCCCCCCCC(CCCCCC)COCC(CC)CCCC] |
| GE21 | 382.71 | $C_{26}H_{54}O$ | 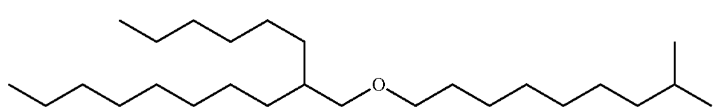 [SMILES: CCCCCCCCC(CCCCCC)COCCCCCCCC(C)C] |
| GE22 | 410.76 | $C_{28}H_{58}O$ | 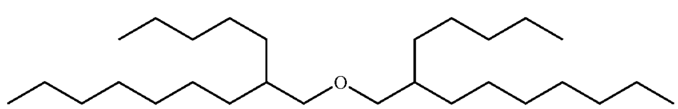 [SMILES: CCCCCCCC(CCCCC)COCC(CCCCC)CCCCCCC] |
| GE23 | 382.71 | $C_{26}H_{54}O$ | 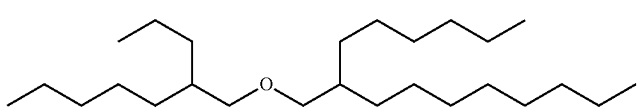 [SMILES: CCCCCCCCC(CCCCCC)COCC(CCC)CCCCC] |

TABLE 3-continued

| | Molecular Weight | Chemical Formula | Structure |
|---|---|---|---|
| SE1 | 452.84 | $C_{31}H_{64}O$ | 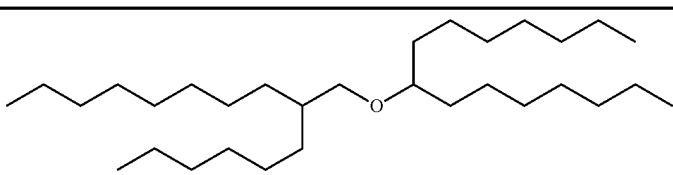 |
| SE2 | 396.43 | $C_{27}H_{56}O$ | 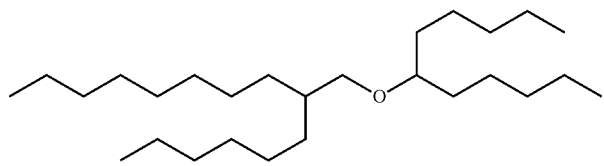 [SMILES: CCCCCCCCC(CCCCCC)COC(CCCCC)CCCCC] |
| TE1 | 466.87 | $C_{32}H_{66}O$ | 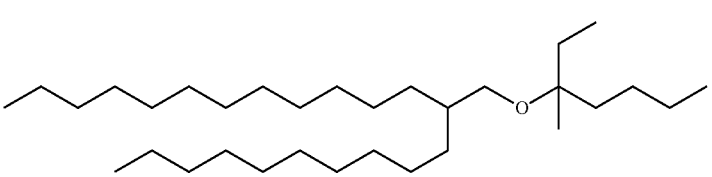 [SMILES: CCCCCCCCCCCCC(CCCCCCCCCC)COC(C)(CC)CCCC] |
| Farnesene-derived ether | 396.73 | $C_{27}H_{56}O$ | 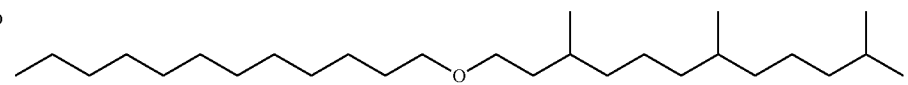 |

The following properties of the base stocks were tested:

Kinematic viscosity at 100° C. (KV100) and kinematic viscosity at 40° C. (KV40) were tested according to ASTM D7279.

Viscosity index (VI) was calculated according to ASTM D2270.

Pour point was determined according to ASTM D7346.

Differential scanning calorimetry (DSC) oxidation onset temperature was tested using a method which was based on ASTM E2009 (method B). According to the method, the base stocks were heated from 50° C. to 300° C., at a rate of 50° C./minute, under a pressure of 500 psi in an aluminium SFI pan. The temperature at which an exotherm was observed was recorded.

Noack volatility was measured using a method which was based on IP 393 and was considered similar to CEC-L-40-A-93. According to the method, reference oils of known Noack volatility were heated from 40° C. to 550° C. to determine the temperature at which the Noack volatility weight loss of each of the reference oils was reached. The base stocks were subjected to the same process as the reference oils. The Noack weight of the base stocks could be determined based on the results obtained from the reference oils.

The results of the tests are summarized in Table 4, together with results obtained from conventional base stocks (Durasyn 162, a group IV base stock; Durasyn 164, a group IV base stock; Yubase 3, a group II base stock; Yubase 4, a group III base stock; Yubase 4 Plus, a group III base stock; Nexbase 3020, a group II base stock; Nexbase 3030, a group II base stock; Nexbase 3043, a group III base stock; and Chevron 100RLV, a group II base stock). Results obtained from the farnesene-derived ether base stock are also shown for reference.

TABLE 4

| | KV100 (cSt) | KV40 (cSt) | VI | Pour Point (° C.) | DSC Oxidation Onset T (° C.) | Noack (% by weight) |
|---|---|---|---|---|---|---|
| GE1 | 3.3 | 13.0 | 125 | −42 | 201.26 | 5.9 |
| GE2 | 3.5 | 13.7 | 145 | −36 | 205.74 | 5.1 |
| GE3 | 3.9 | 16.0 | 143 | −42 | 202.89 | 2.4 |
| GE4 | 3.3 | 11.9 | 146 | −27 | 213.37 | 3.9 |
| GE5 | 2.5 | 8.2 | 136 | −60 | 203.87 | 17.9 |
| GE6 | 3.8 | 14.6 | 166 | −12 | 212.71 | 2.0 |
| GE7 | 4.0 | 16.5 | 144 | −36 | 206.26 | 6.8 |
| GE8 | 2.3 | 7.7 | 111 | −66 | 213.95 | 44.9 |
| GE9 | 3.8 | 14.9 | 160 | −15 | 208.17 | 2.5 |
| SE1 | 2.7 | 9.6 | 123 | −18 | 195.37 | 12.9 |
| SE2 | 2.5 | 9.0 | 101 | −45 | 183.21 | 51.8 |
| TE1 | 3.6 | 14.9 | 133 | — | 212.91 | 6.8 |
| Durasyn 162 | 1.7 | 5.2 | 92 | −72 | 223.61 | 99.6 |
| Durasyn 164 | 4.0 | 17.8 | 126 | −75 | 221.31 | 18.8 |
| Yubase 3 | 3.0 | 14.1 | 105 | −36 | 220.74 | 38.6 |
| Yubase 4 | 4.2 | 19.2 | 126 | −12 | 220.00 | 11.7 |
| Yubase 4 Plus | 4.2 | 18.4 | 138 | −18 | 220.32 | 11.6 |
| Nexbase 3020 | 2.2 | 7.6 | 93 | −51 | 221.66 | 81.9 |
| Nexbase 3030 | 3.0 | 12.0 | 101 | −39 | 221.05 | 36.8 |
| Nexbase 3043 | 4.3 | 19.9 | 124 | −18 | 222.09 | 13.2 |
| Chevron 110RLV | 4.6 | 22.6 | 119 | −15 | 225.86 | 13.2 |
| Farnesene-derived ether | 3.2 | 11.6 | 152 | −36 | 222.26 | 14.1 |

Figure 1:
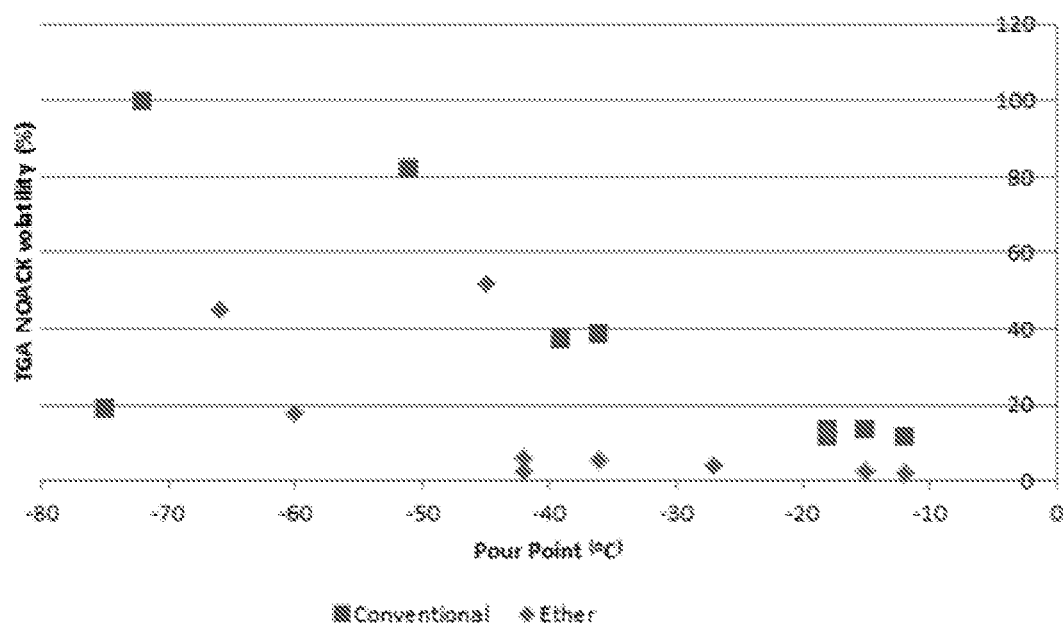
FIG. 1 is a graph of volatility against pour point for compounds of formula (1), other ether base stocks and conventional base stocks.

A graph of volatility against pour point for ether base stocks GE1-GE9, SE1, SE2 and TE1 and the conventional base stocks is shown in FIG. 1. It can be seen that the Guerbet-derived base stock ethers have a low volatility for a given pour point compared to conventional base oils. Moreover, the Guerbet-derived base stocks in which both sides of the ether are branched exhibit unexpected improvements in pour point as compared to Guerbet-derived base stocks of comparable carbon number in which only one side of the ether is branched, without any significant loss of volatility.

Figure 2:
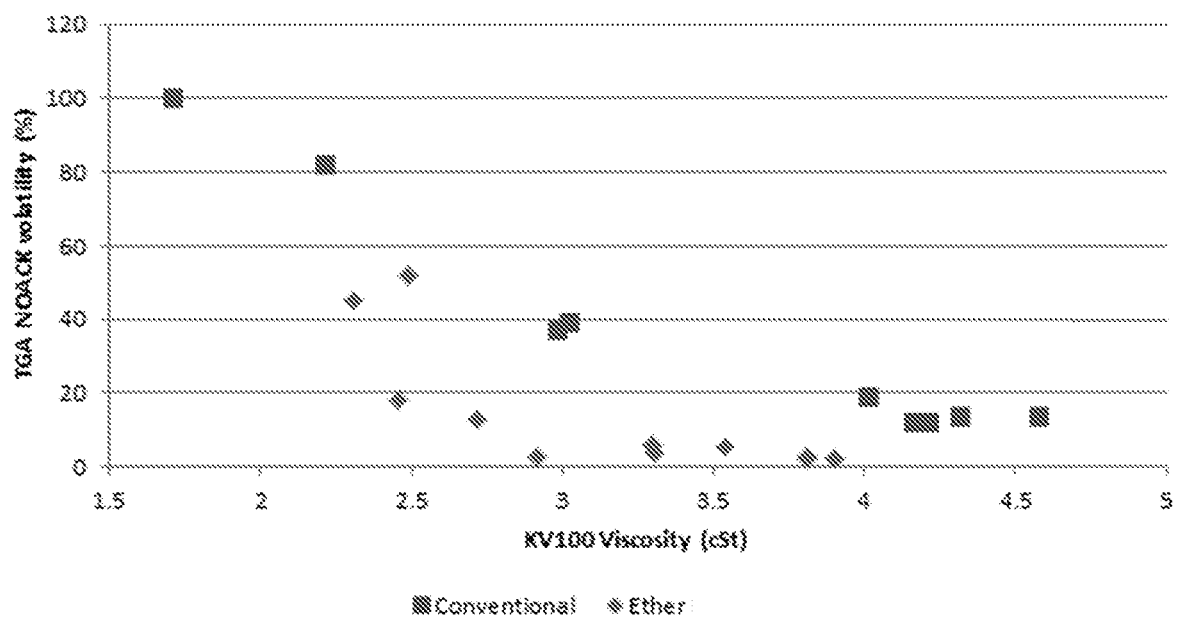
FIG. 2 is a graph of volatility against kinematic viscosity at 100° C. for compounds of formula (1), other ether base stocks and conventional base stocks.

A graph of volatility against kinematic viscosity at 100° C. for ether base stocks GE1-GE9, SE1, SE2 and TE1 and the conventional base stocks is shown in FIG. 2. It can be seen that the Guerbet-derived base stocks and the secondary and tertiary ether base stocks exhibit both low volatility and low viscosity as compared to conventional base oils.

Figure 3:
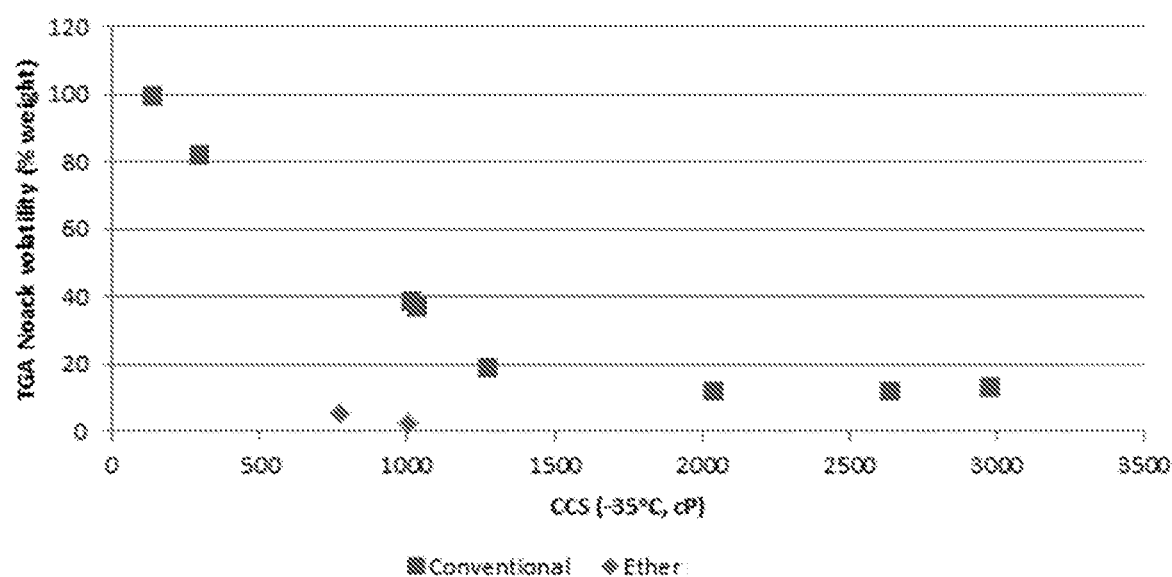
FIG. 3 is a graph of volatility against cold-cranking simulator performance for compounds of formula (1) and conventional base stocks.

Cold-cranking simulator (CCS) analysis of Guerbet-derived base stocks GE2 and GE3 was also carried out according to ASTM D5293. A graph of volatility against cold-cranking simulator viscosity is shown in FIG. 3. For comparison, data obtained from conventional hydrocarbon base stocks having a KV100 of from 2.6 to 4.2 is also shown. It can be seen that the Guerbet-derived ethers exhibit excellent CCS viscosity, as well as low volatility.

Example 2: Properties of Lubricant Compositions Containing Ether Base Stocks

Guerbet-derived ether base stocks GE2 and GE3 were blended with conventional base oil additives (additive A, a commercially available additive package; additive B, a cold-flow improver; additive C, an oxidation inhibitor; and additive D, a viscosity index improver) and conventional base oils (Yubase 4, a group III base oil; and Yubase 6, a group III base oil) to form lubricant blends. A Baseline blend and a farnesene-derived ether blend were also prepared. Yubase 4 was chosen as the main component of the Baseline blend, since it exhibits a similar KV100 to Guerbet-derived ether base stock, GE3. The Baseline blend was believed to be a stringent baseline for comparison, since it is a 5W-30 formulation which meets certain specifications (ACEA A5/B5, API-SN/GF-4). The details of the blended compositions are shown in Table 5 in % by weight.

TABLE 5

| | Baseline blend | GE2 blend | GE3 blend | Farnesene-derived blend |
|---|---|---|---|---|
| Additive A | 16.4 | 16.4 | 16.4 | 16.4 |
| Additive B | 0.15 | 0.15 | 0.15 | 0.15 |
| Additive C | 0.1 | 0.1 | 0.1 | 0.1 |
| Additive D | 4 | 4 | 4 | 4 |
| Yubase 4 | 67.45 | 30.47 | 17.45 | 17.45 |
| Yubase 6 | 11.9 | 11.9 | 11.9 | 11.9 |
| GE2 | 0 | 36.98 | 0 | 0 |
| GE3 | 0 | 0 | 50 | 0 |
| Farnesene-derived ether | 0 | 0 | 0 | 50 |

No problems with miscibility were encountered during preparation of the blended compositions.

The blended compositions were tested to see whether the advantageous properties of the base stocks would be reflected in a fully formulated lubricant composition. The following properties were tested:

Kinematic viscosity at 100° C. (KV100) and kinematic viscosity at 40° C. (KV40) were tested according to ASTM D445 (part of SAE J300).

Viscosity index (VI) was calculated according to ASTM D2270.

Cold-cranking simulator (CCS) analysis was carried out at −30° C. according to ASTM D5293 (part of SAE J300).

High temperature high shear (HTHS) analysis was carried out according to CEC-L-36-A-90.

Total base number (TBN) was determined according to ASTM D2896.

Noack volatility was tested according to CEC-L-40-A-93.
Sulphated ash content was measured according to IP 163.
The results of the tests are summarized in Table 6.

TABLE 6

| | Baseline blend | GE2 blend | GE3 blend | Farnesene-derived blend |
|---|---|---|---|---|
| KV40 (cSt) | 53.59 | 48.26 | 44.63 | 38.57 |
| KV100 (cSt) | 9.542 | 9.105 | 8.688 | 7.877 |
| VI | 164 | 173 | 177 | 181 |
| CCS −30° C. (cP) | 4656 | 2608 | 2702 | 2010 |
| HTHS (cP) | 2.98 | 2.85 | 2.75 | 2.62 |
| TBN (mg KOH/g) | 11.66 | 11.29 | 11.44 | 10.88 |
| NOACK (% by weight) | 11.2 | 7.7 | 9.7 | 14.9 |
| Sulphated ash (%) | 1.22 | 1.26 | 1.27 | 1.20 |

It can be seen that the properties of the Guerbet-derived base stocks are also exhibited in the blended compositions. In particular, beneficial viscosity, volatility and cold-flow properties are observed. The Guerbet-derived base stocks also exhibited similar HTHS measurements, TBNs and sulphated ash contents to the Baseline blend.

Example 3: Engine Performance of Lubricant Compositions Containing Ether Base Stocks The blended compositions from Example 2 were subjected to a TU-5 JP engine test run according to CEC-L-88-02 (part of ACEA A, B and C sequences) in order to determine the oxidative stability of the compositions by assessment of viscosity increases, as well as piston cleanliness and piston ring sticking. The temperature in the oil gallery was controlled to 150° C. for the duration of the test. The results of the TU-5 JP engine tests for the Baseline, GE2 and GE3 lubricant compositions are shown in Table 7.

The blended compositions from Example 2 were also subjected to MRV testing at −35° C. according to ASTM D4684 in order to gauge low-temperature viscosity characteristics of the compositions before and after use in the TU-5 JP engine test. The results of the MRV testing are also shown in Table 7.

TABLE 7

| | Baseline | GE2 | GE3 | Limits |
|---|---|---|---|---|
| Absolute viscosity increase at 40° C. (mm²/s) | 47.3 | 27 | 13.1 | ≤57.3 |
| Viscosity at 40° C. 0 hours (mm²/s) | 53.8 | 45.1 | 48.2 | None |
| Viscosity at 40° C. 72 hours (mm²/s) | 101.1 | 72.1 | 61.3 | None |
| Overall piston merit (x/10) (5 elements, CRC rating) | 8.2 | 9.2 | 9.0 | >7.6 |
| Ring sticking merit 1st ring (worst) | 10 | 10 | 10 | ≥9 |
| MRV pre-TU-5 (cP) | 21500 | 7200 | 7500 | |
| Yield stress pre-TU-5 (Pa) | <35 | <35 | <35 | |
| MRV post-TU-5 (cP) | 56500 | 11700 | 18000 | |
| Yield stress post-TU-5 (Pa) | <35 | <35 | <35 | |

The lubricant compositions containing Guerbet-derived base stocks passed all aspects of the TU-5 JP engine test.

A graph of kinematic viscosity at 40° C. against time is shown in FIG. 4a, and a graph showing the absolute change in kinematic viscosity at 40° C. after 60 hours is shown in FIG. 4b. For comparison, results obtained from the Farnesene-derived blend from Example 2 are also shown. It can be seen that the increase in viscosity of the lubricant compositions containing Guerbet-derived base stocks or the Farnesene-derived blend were significantly lower than or similar to that of the Baseline composition, with the results obtained from the Guerbet-derived ether being particularly good. The results indicate that the lubricant compositions containing ether base stocks exhibit superior oxidative stability.

A graph showing the overall piston merit is shown in FIG. 5. It can be seen that the lubricant compositions containing Guerbet-derived base stocks had overall high piston merits score, indicating that these blends exhibit good piston cleanliness performance.

The MRV results further demonstrate the excellent low-temperature viscosity characteristics of lubricant compositions containing Guerbet-derived base stocks before and after their use.

Example 4: Engine Compatibility of Lubricant Compositions Containing Ether Base Stocks The blended formulation of GE3 from Example 2 was subjected to Mercedes EAM and ACEA RE2 seal tests (test methods VDA 675301 and CEC-L-39-96, respectively) to determine the compatibility of the ether base stocks with typical seals that are found in engines. An ethylene acrylic rubber is used in the EAM test, whilst an acrylic-based rubber is used in the RE2 test. The results of the Mercedes EAM and ACEA RE2 seal tests are shown in Table 8.

TABLE 8

| | | Baseline | GE3 | Pass Limits |
|---|---|---|---|---|
| AEM Seal Test | Tensile strength (Mpa % variation) | 9.5 | 3.4 | >−35 |
| | Elongation Rupture (% variation) | −18.6 | −26.9 | >−50 |
| | Hardness (Variation, points) | 3 | 5 | 10 to −5 |
| | Relative volume change (%) | 2.5 | 0.3 | 15 to −5 |
| ACEA RE2 | Tensile Strength (% variation) | 2 | 2 | 18 to −15 |
| | Elongation Rupture (% variation) | −32 | −35 | 10 to −35 |
| | Hardness (Variation, points) | 7 | 3 | 8 to −5 |
| | Relative volume change (%) | 0.6 | 0.6 | 5 to −7 |

It can be seen that the lubricant composition containing a Guerbet-derived base stock passed both of the seal tests, indicating that the ether base stocks are suitable for use in engines.

Example 5: Engine Fuel Consumption Performance of Lubricant Compositions Containing Ether Base-Stocks Another blended formulation of GE3 and the baseline blend were subjected to an M111 fuel economy test according to CEC-L-054-96 (part of the ACEA A and B sequences) in order to determine the fuel consumption performance of engines run on ether base-stocks. The results are given below in table 9 and are quoted as percentage improvement over the RL191 15W-40 baseline oil commonly used for such assessments. Accordingly, the results reported as "Baseline" below recite the percentage performance of the Baseline blend (5W-30 formulation mentioned above) over the RL 191 15W-40 standard.

TABLE 9

| | Baseline | GE3 | Pass Limits |
|---|---|---|---|
| Fuel Economy Improvement relative to RL191 15W-40 | 2.89% | 3.19% | >2.5% |

It can be seen that the lubricant containing a Guerbet-derived base stock passed the fuel economy test and showed an improvement over the baseline lubricant composition, indicating that the ether base stocks offer a fuel economy benefit.

The invention claimed is:

1. A lubricant composition comprising a base oil comprising a compound of formula (2),

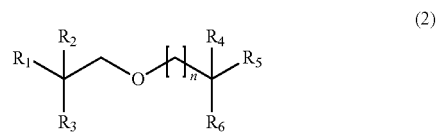

(2)

where: $R_1$ and $R_2$ are alkyl or, together with the carbon atom to which they are attached, cycloalkyl;
$R_3$ and $R_5$ are H or alkyl;
$R_4$ is alkyl;
$R_6$ is alkyl; and
n is 0, 1, 2 or 3,
wherein the compound contains a total number of carbon atoms of from 20 to 50, and wherein the lubricant composition has at least one of:
an oxidative stability performance on a CEC-L-088-02 test indicated by an absolute viscosity increase at 40° C. of no more than 45 cSt;
a fuel economy performance on a CEC-L-054-96 test of at least 2.5%; and
a piston cleanliness performance on a CEC-L-088-02 test indicated by an overall piston merit of at least 8.5.

2. A method of improving the fuel economy performance and/or piston cleanliness performance of an engine and/or a vehicle, comprising the step of providing to the engine and/or the vehicle a compound of formula (2),

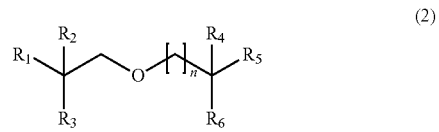

(2)

where: $R_1$ and $R_2$ are alkyl or, together with the carbon atom to which they are attached, cycloalkyl;
$R_3$ and $R_5$ are H or alkyl;
$R_4$ is alkyl;
$R_6$ is alkyl; and
n is 0, 1, 2 or 3,
wherein the compound contains a total number of carbon atoms of from 20 to 50.

3. A method of improving the fuel economy performance and/or piston cleanliness performance of an engine and/or a vehicle, comprising the step of providing to the engine and/or the vehicle a base oil comprising a compound of formula (2),

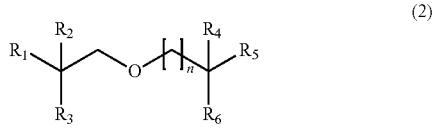

where: $R_1$ and $R_2$ are alkyl or, together with the carbon atom to which they are attached, cycloalkyl;
$R_3$ and $R_5$ are H or alkyl;
$R_4$ is alkyl;
$R_6$ is alkyl; and
n is 0, 1, 2 or 3,
wherein the compound contains a total number of carbon atoms of from 20 to 50.

4. A method of improving the fuel economy performance and/or piston cleanliness performance of an engine and/or a vehicle, comprising the step of providing to the engine and/or the vehicle a lubricating composition comprising a base oil comprising a compound of formula (2),

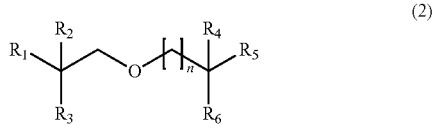

where: $R_1$ and $R_2$ are alkyl or, together with the carbon atom to which they are attached, cycloalkyl;
$R_3$ and $R_5$ are H or alkyl;
$R_4$ is alkyl;
$R_6$ is alkyl; and
n is 0, 1, 2 or 3,
wherein the compound contains a total number of carbon atoms of from 20 to 50.

5. The lubricant composition of claim 1, wherein
$R_1$ and $R_2$ are $C_{1-15}$ alkyl or, together with the carbon atom to which they are attached, $C_{5-30}$ cycloalkyl;
$R_3$ and $R_5$ are H or $C_{1-15}$ alkyl;
$R_4$ is $C_{1-15}$ alkyl;
$R_6$ is $C_{1-15}$ alkyl; and
n is 0, 1, or 2.

6. The lubricant composition of claim 1, wherein
$R_1$ and $R_2$ are $C_{2-12}$ alkyl or, together with the carbon atom to which they are attached, $C_{5-25}$ cycloalkyl;
$R_3$ and $R_5$ are H or $C_{2-12}$ alkyl;
$R_4$ is $C_{2-12}$ alkyl;
$R_6$ is $C_{2-12}$ alkyl; and
n is 0, 1, or 2.

7. The lubricant composition of claim 1, wherein
$R_1$ and $R_2$ are $C_{2-12}$ alkyl or, together with the carbon atom to which they are attached, $C_{5-25}$ cycloalkyl;
$R_3$ is H or $C_{2-12}$ alkyl;
$R_4$ is $C_{2-12}$ alkyl;
$R_5$ is H;
$R_6$ is $C_{2-12}$ alkyl; and
n is 0 or 1.

8. The lubricant composition of claim 1, wherein:
$R_1$ is $C_{6-10}$ alkyl;
$R_3$ is H;
$R_4$ is $C_{2-8}$ alkyl; and
$R_5$ is H.

9. The lubricant composition of claim 1, wherein the lubricant composition comprises greater than 50% by weight of the base oil.

10. The lubricant composition of claim 1, wherein the lubricant composition has at least one of:
a kinematic viscosity at 40° C. of less than 60 cSt;
a kinematic viscosity at 100° C. of less than 12 cSt;
a viscosity index of greater than 100;
a viscosity at 150° C. and a shear rate of $10^6$ $s^{-1}$ of no greater than 3 cP; and
a Noack volatility of less than 25% by weight.

11. The lubricant composition of claim 1, wherein the compound has the formula (3):

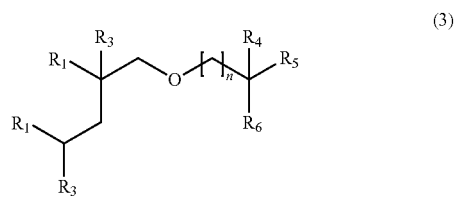

where: $R_1$ is alkyl;
$R_3$ and $R_5$ are H or alkyl;
$R_4$ is alkyl;
$R_6$ is alkyl; and
n is 0, 1, 2 or 3.

12. The lubricant composition of claim 1, wherein the compound has the formula (4):

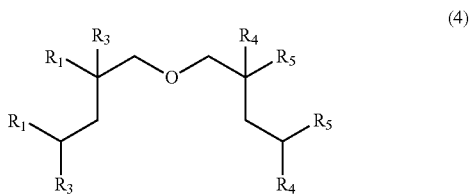

where: $R_1$ and $R_4$ are $C_{1-15}$ alkyl;
$R_3$ and $R_5$ are H or $C_{1-15}$ alkyl.

13. The lubricant composition of claim 12, wherein:
$R_1$ is $C_{4-12}$ alkyl;
$R_3$ is H;
$R_4$ is $C_{1-10}$ alkyl; and
$R_5$ is H.

14. The lubricant composition of claim 1, wherein the compound has the formula (10):

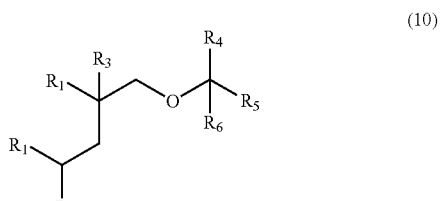

where: $R_1$ and $R_4$ are alkyl;
$R_3$ and $R_5$ are H or alkyl;
$R_6$ is alkyl.

15. The lubricant composition of claim 1, wherein the compound contains greater than 50% by weight of biobased carbon.

16. The lubricant composition of claim 1, wherein the compound has at least one of:
 a kinematic viscosity at 40° C. of less than 25 cSt;
 a kinematic viscosity at 100° C. of less than 7 cSt;
 a viscosity index of greater than 100;
 a viscosity at 150° C. and a shear rate of $10^6$ $s^{-1}$ of no greater than 1.7 cP;
 a Noack volatility of less than 26% by weight; and
 a pour point of less than −10° C.

17. The lubricant composition of claim 1, wherein the base oil comprises greater than 10% by weight of the compound.

18. The method of claim 2, wherein the compound has the formula (3):

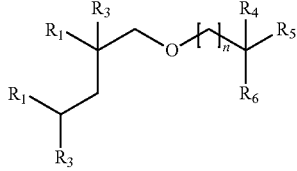

(3)

where: $R_1$ is alkyl;
 $R_3$ and $R_5$ are H or alkyl;
 $R_4$ is alkyl;
 $R_6$ is alkyl; and
 n is 0, 1, 2 or 3.

19. The method of claim 2, wherein the compound has the formula (4):

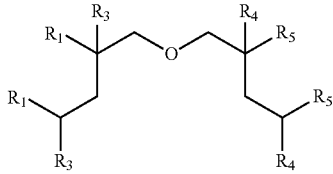

(4)

where: $R_1$ and $R_4$ are $C_{1-15}$ alkyl;
 $R_3$ and $R_5$ are H or $C_{1-15}$ alkyl.

20. The method of claim 2, wherein:
 $R_1$ is $C_{4-12}$ alkyl;
 $R_3$ is H;
 $R_4$ is $C_{1-10}$ alkyl; and
 $R_5$ is H.

21. The method of claim 2, wherein the compound has the formula (10):

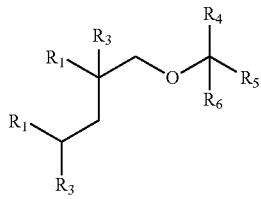

(10)

where: $R_1$ and $R_4$ are alkyl;
 $R_3$ and $R_5$ are H or alkyl;
 $R_6$ is alkyl.

22. The method of claim 2, wherein the compound contains greater than 50% by weight of biobased carbon.

23. The method of claim 2, wherein the compound has at least one of:
 a kinematic viscosity at 40° C. of less than 25 cSt;
 a kinematic viscosity at 100° C. of less than 7 cSt;
 a viscosity index of greater than 100;
 a viscosity at 150° C. and a shear rate of $10^6$ $s^{-1}$ of no greater than 1.7 cP;
 a Noack volatility of less than 26% by weight; and
 a pour point of less than −10° C.

24. The method of claim 3, wherein the compound has the formula (3):

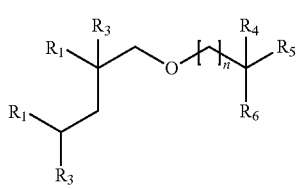

(3)

where: $R_1$ is alkyl;
 $R_3$ and $R_5$ are H or alkyl;
 $R_4$ is alkyl;
 $R_6$ is alkyl; and
 n is 0, 1, 2 or 3.

25. The method of claim 3, wherein the compound has the formula (4):

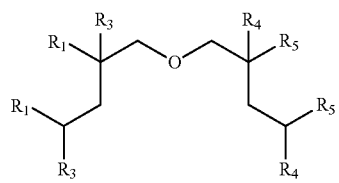

(4)

where: $R_1$ and $R_4$ are $C_{1-15}$ alkyl;
 $R_3$ and $R_5$ are H or $C_{1-15}$ alkyl.

26. The method of claim 3, wherein:
 $R_1$ is $C_{4-12}$ alkyl;
 $R_3$ is H;
 $R_4$ is $C_{1-10}$ alkyl; and
 $R_5$ is H.

27. The method of claim 3, wherein the compound has the formula (10):

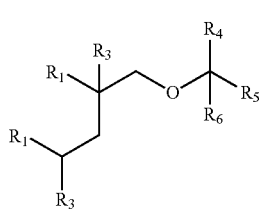

(10)

where: $R_1$ and $R_4$ are alkyl;
 $R_3$ and $R_5$ are H or alkyl;
 $R_6$ is alkyl.

28. The method of claim 3, wherein the compound contains greater than 50% by weight of biobased carbon.

29. The method of claim 3, wherein the compound has at least one of:
- a kinematic viscosity at 40° C. of less than 25 cSt;
- a kinematic viscosity at 100° C. of less than 7 cSt;
- a viscosity index of greater than 100;
- a viscosity at 150° C. and a shear rate of $10^6$ $s^{-1}$ of no greater than 1.7 cP;
- a Noack volatility of less than 26% by weight; and
- a pour point of less than −10° C.

30. The method of claim 3, wherein the base oil comprises greater than 10% by weight of the compound.

31. The method of claim 3, wherein the compound contains greater than 50% by weight of biobased carbon.

32. The method of claim 4, wherein the lubricant composition comprises greater than 50% by weight of the base oil.

\* \* \* \* \*